(12) United States Patent
Tabe

(10) Patent No.: US 7,271,720 B2
(45) Date of Patent: Sep. 18, 2007

(54) HOMELAND INTELLIGENT SYSTEMS TECHNOLOGY "H-LIST"

(76) Inventor: Joseph Tabe, 525 Thayer Ave., Suite 315, Silver Spring, MD (US) 20910

( * ) Notice: Subject to any disclaimer, the term of this patent is extended or adjusted under 35 U.S.C. 154(b) by 93 days.

(21) Appl. No.: 10/660,473

(22) Filed: Sep. 12, 2003

(65) Prior Publication Data

US 2004/0138829 A1 Jul. 15, 2004
US 2004/0220753 A1 Nov. 4, 2004

Related U.S. Application Data

(60) Provisional application No. 60/426,800, filed on Nov. 18, 2002.

(51) Int. Cl.
*G08B 21/00* (2006.01)
(52) U.S. Cl. ............... 340/540; 340/541; 340/539.12; 340/573.1; 340/632; 340/506
(58) Field of Classification Search .............. 340/540, 340/539.11, 425.5, 539.26, 539.12, 573.1, 340/426.11, 426.15, 632, 506, 870.01, 541
See application file for complete search history.

(56) References Cited

U.S. PATENT DOCUMENTS

| | | | | |
|---|---|---|---|---|
| 5,065,140 | A * | 11/1991 | Neuburger | 340/634 |
| 6,198,394 | B1 * | 3/2001 | Jacobsen et al. | 340/573.1 |
| 6,842,009 | B2 * | 1/2005 | Potter | 324/633 |
| 2004/0015336 | A1 * | 1/2004 | Kulesz et al. | 703/11 |

* cited by examiner

Primary Examiner—Tai Nguyen

(57) ABSTRACT

Homeland Intelligence Systems Technology "H-LIST" comprises nano-sensors embedded in a silicon substrate and etched/fused in a micro-fibered material to enable an outfit for monitoring suspicious terrorist activities and for track biological and chemical gases, and explosives, including stationary and portable weapons of mass destruction such as those that are likely carried on the body of a terrorist or suicide bomber, or that are likely planted in a parked vehicle or carried inside a moving vehicle. H-LIST includes a wired outfit comprising at least a jacket that is worn by an officer, a security officer, a bus driver, hostesses, Doctors and the like, for sensing deadly gases and explosives in a defined area. A receptor is operatively configured with the outfit and attached on a waist belt, and communicatively connected to the outfit input/output connector through at least wired or wirelessly means for empowering the sensors and for receiving signal communication wirelessly; indicating the presence of a sensed agent. Detected signals are transported wirelessly through radio frequency signals to a central security monitoring station, enabling communication with first responders and backup security personnel or agents to the vicinity of the detection. The sensors are multifunctional and coded to recognize wavelike pattern of gases and explosives traveling through wave. The wired outfit and the receptor are operable to process the portion of the detection signal to determine whether there is a concealed object by conducting a test in which a first characteristic of a first dielectric constant associated with a person is determined, and a second characteristic of a second dielectric constant associated with the concealed object and or weapons of mass destruction is determined to expedite data transmission and communication to first responders.

45 Claims, 17 Drawing Sheets

FIG. 1

FIGURE 6   BLOCK DIAGRAM OF A RECEPTOR PERFORMANCE HARDWARE

FIG. 7     DETECTION ARRAY

FIGURE 8     RECEPTOR PRIVACY INDICATOR

WIND TOWER ON A MILITARY SHIP

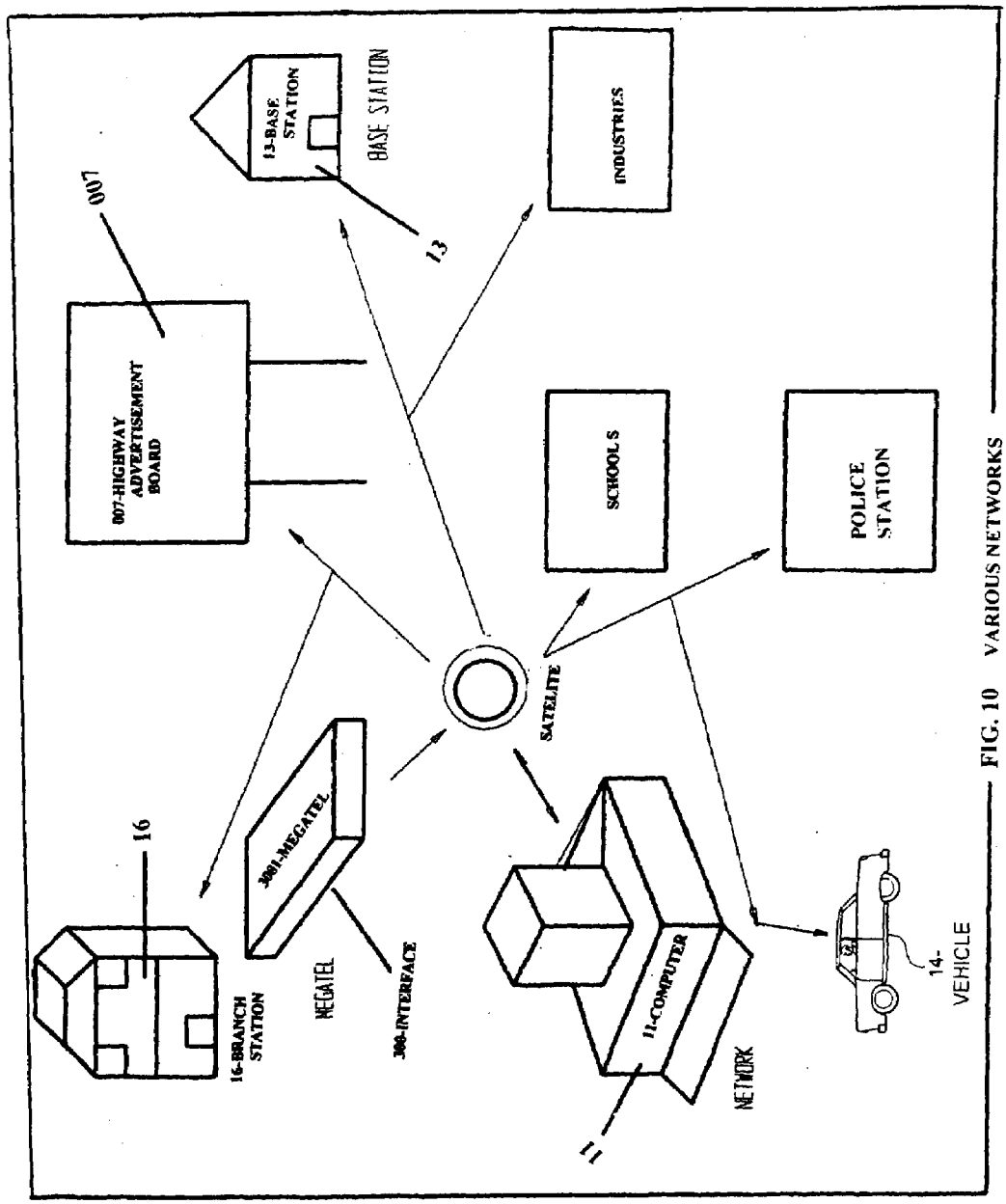
FIG. 10 VARIOUS NETWORKS

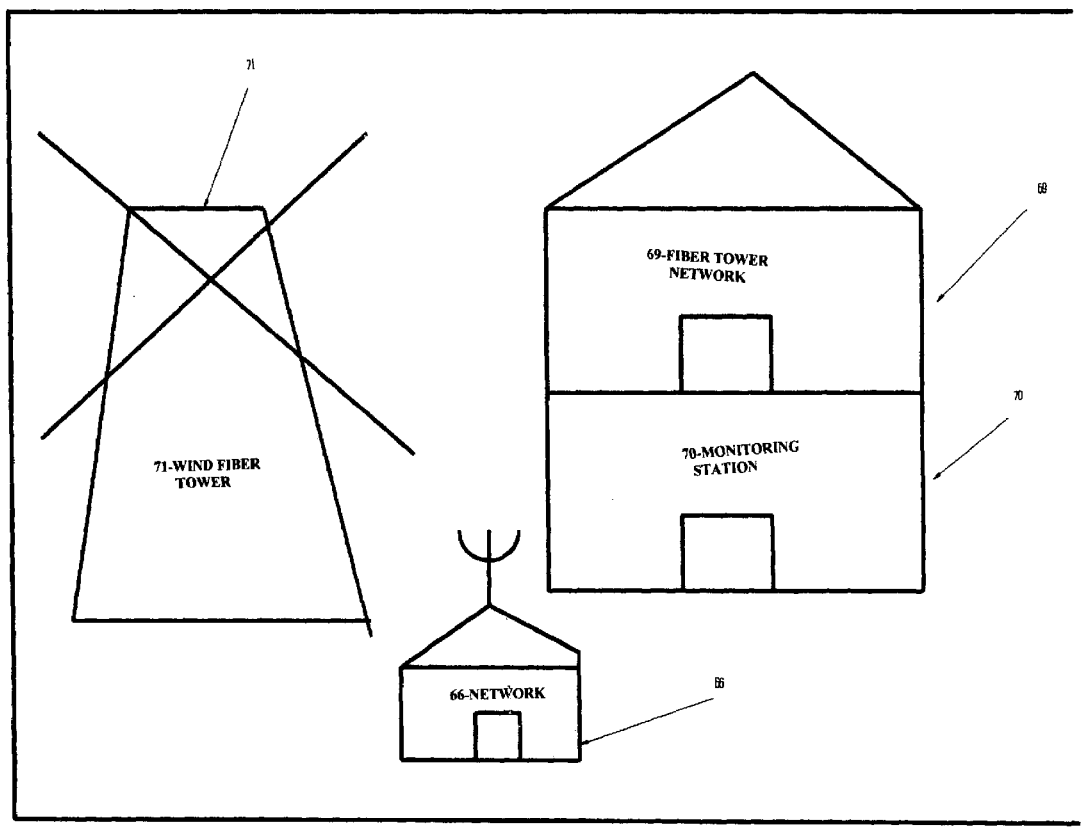
FIGURE 11   NETWORK ENVIRONMENT

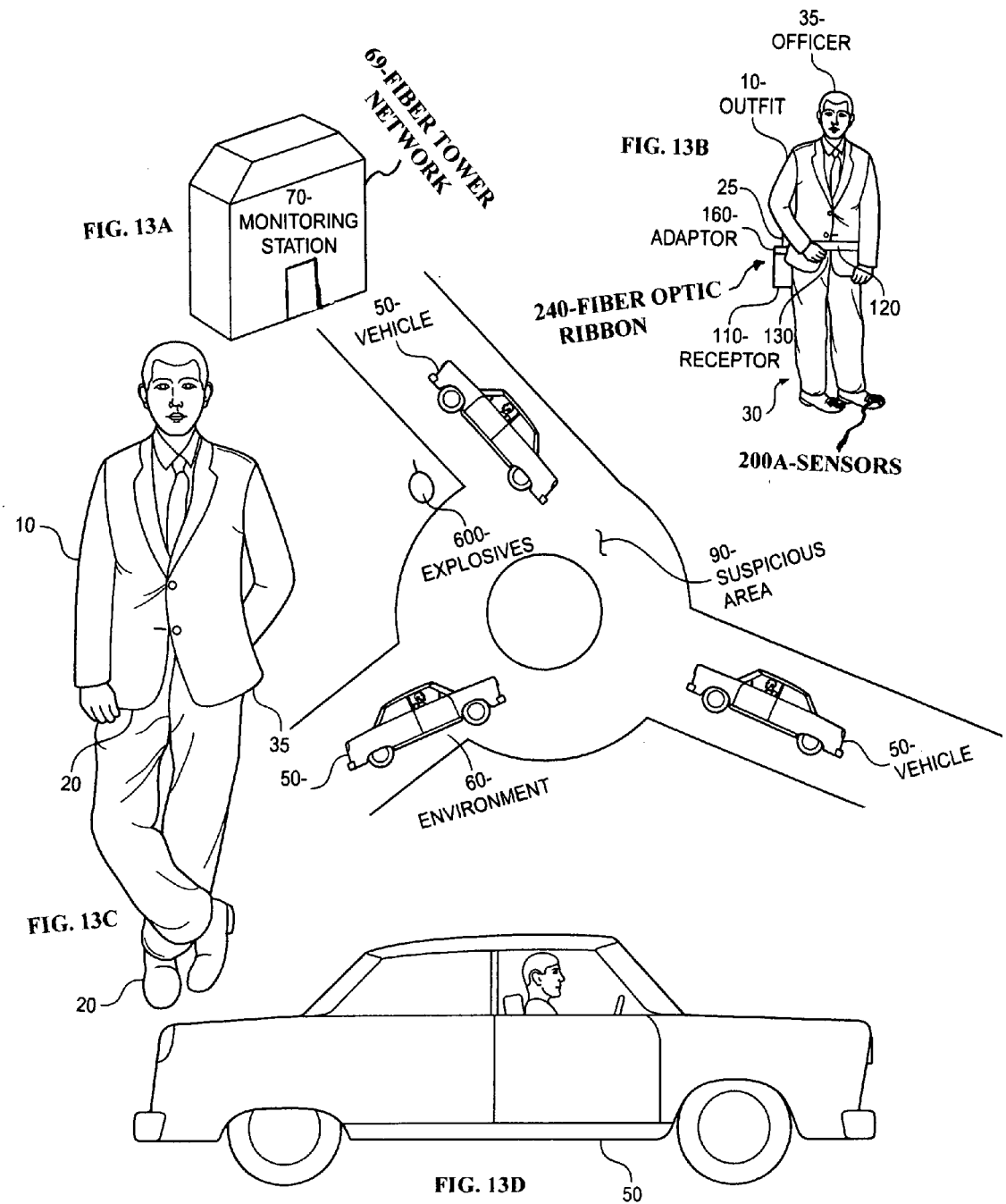

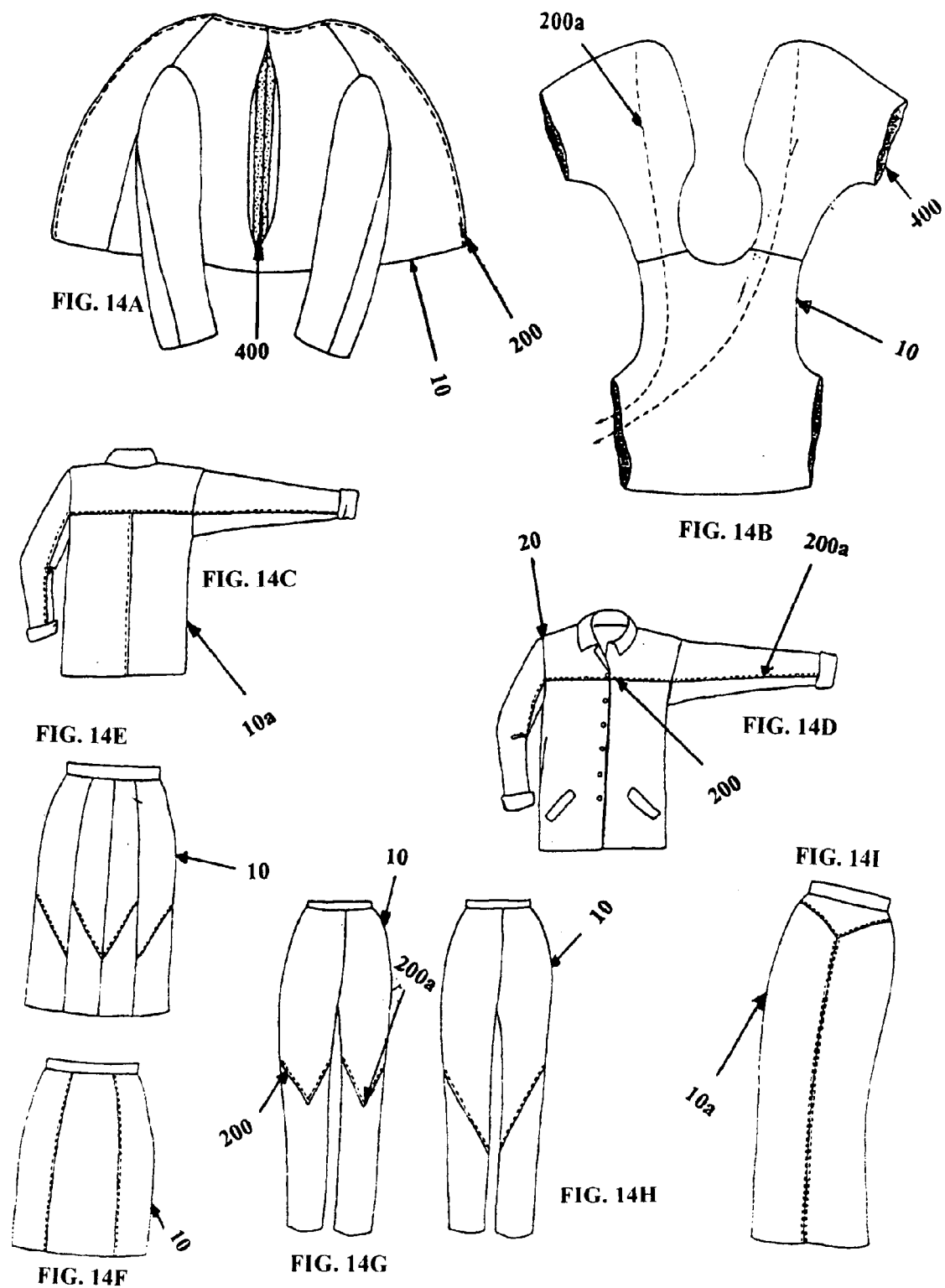
FIG. 14 DIFFERENT COMBINATIONS OF OUTFIT DESIGNS

HOMELAND INTELLIGENT SYSTEMS TECHNOLOGY "H-LIST"

This application claims benefit from a provisional application Ser. No. 60/426,800, filed Nov. 18, 2002.

PURPOSE

Enable digital combat on a battlefield

To advance homeland security technology into randomly patrolled mobile system

To keep airport perimeters and access under secured security control system

Safeguard personnel against bacteria caused by the launching of weapons of mass destruction.

To reduce the hassles involved in airport securities and procedures while also improving and safeguarding the lives of occupants.

To monitor battlefield personnel, their heartbeat, and their respiratory system to monitor battlefield enemies, their movements, and the location of their weapons.

Enables wireless digital network for homeland security and army personnel.

To advance technologies that will enable flight attendants to self-protect the safety of an aircraft and its occupants.

Improve homeland security standard when defending an assigned area of the building.

To improve security standards on transit trains, trucks, buses and the like.

Besides barriers or security guards, drivers will safeguard their buses against explosives, chemical or biological agents, and drugs such as narcotics.

Nuclear power plants access restriction will be better safguarded.

To improve security standards on power plants such as nuclear power plant and the like.

To enable innovative military advanced combat system.

To enable detection of weapons of mass destruction or when a chemical or biological gas has been used in a battlefield, it ensures timely evacuation of the area so affected.

To enable detection of anthrax spore, bacterial, fungal spores, and viruses

FIELD OF THE INVENTION

A Homeland Intelligence Systems Technology "H-LIST" for monitoring homeland security and the like includes a wearable outfit or jacket with detachable interior for thermal insulation and wireless communication through its receptors that are optionally knowledgeable and communicative such that deadly and explosive devices are detected by the outfit and the detection information is communicated through sensors on the outfit or jacket insulators to the attached receptor connected on the said outfit to enable amplified wireless communication thereon. The outfit protects the body against body bacteria from weapons of mass destruction and also takes pulse and respiratory data of personnel, enabling the receptor to report all communicative data and detected information to the central security reporting stations or network. The stations or network have interactive links with other law enforcement networks to enable instant response to anticipatory attack

BACKGROUND OF THE INVENTION

Previous biological, chemical, and explosive detection devices have been developed and mounted on fixed positions to perform their assigned tasks, such as locating explosive devices through sensors at the gateway of airports, or doorway of government buildings. Still, some undetected explosives have been used to blow off planes and buses because some how, the prior devices failed to detect the explosives at the time they were un-wrapped from their carefully sealed plastics. Other detection devices are so disturbing when used on their portable environment around the airport and government buildings to detect weapons of mass destruction on ones body. More so, terrorist groups are expanding the act of suicide bombing technologies, which are strategically planned for and carried on the public streets, public transportations, recreational environments, or outside some government buildings. With the suicide bomber's strategic selection of key targets and location to perform such deadly acts, current detection system has no way of sensing that a parked car with explosives and the like is in front of any of these locations waiting to be activated.

Some technologies are focusing more on only signal interception, but have no way of detecting an explosive that is in a parked car, or on the body of a person entering a bus, or on the body of a person who carefully sealed such device and successfully finds his way inside an air plane, or already used deadly gases on a battle field such that is not visible after a chemical or biological weapon has been launched, or explosive that has successfully gotten inside a stadium on a super bowl game and just waiting to be activated. The present invention advances the intelligence of homeland security in that, it is portable and allows mobile detection of explosives and deadly gases in a person's body, or inside a parked car on the street. The applicant acknowledges that besides fixed or stationed detection machines, homeland security can intelligently protect its environment if the detection devices are mobile, have wireless means to communicate, and can be self carried by security officers.

The applicant also acknowledges that for the device to be self carried and used intelligently, it has to be worn by the security officer at the vicinity of the protective area. Allowing the security officer to patrol an assigned area randomly with the device in his body and alarming thereof if a weapon is detected is another advanced means of approaching the homeland security and the monitoring of our nation. Since biosensors are chemical sensors that take advantage of the high selectivity and sensitivity of a biologically active material, the present invention incorporates an oscillating piezoelectric crystal in the design of a sensor embedded in a security jacket or outfit which is affected by the change in mass on the surface of the crystal due to the resonant frequency of the sensing materials. This sensing material is made of non-ferrous material such as silver and or gold to enable ideal biosensor layer for detection of any liquid, solid, and also gaseous phase explosive detection in their mobile environment. The change in mass occurs when the frequency changes as a result of the environmental condition. The change in mass is measured by a piezoelectric immunosensors, which is then communicated to a receptor.

The receptor eying these biochemical sensors is an analytical tool that consists of biologically active materials such as surface resonance spectroscope and is used with devices that will convert biochemical signal into quantifiable electrical signal to enable communication of all detected information through the electrical signals or pulses traveling in the wire connection between the detecting sensors on the jacket insulator and the receptor. The signals are then transported wirelessly through waves such as radio waves or microwaves, to the central security monitoring stations. Prior devices are limited in their zones and have no way of extending their sensitivity to detecting explosives in a parked car. With the present invention, the area of protective sensing is not limited to the analytical techniques of detecting, polluting, water and microbial contamination analyses, industrial gases and liquids, mining and toxic gases, explosives and military arena; but extends to protecting the airports, transport planes, government buildings, tunnels, city malls, recreational areas, battle field personnel, common buildings and the like. The components of the biochemical sensor for the present invention are not limited to:

(a) A receptor: responsible for the selectivity of a sensor to transform chemical or biological information into energy form which is measured by a transducer. The receptor part is based on physical, chemical, or biochemical principles and functions like an analyzer, sampling responses and transporting said responses through processed signals as a function of time, e.g. enzymes, antibodies, and liquid layers.

(b) A detector: like a transducer, responsible for translating the physical or chemical change by recognizing the analyte and relaying it through electrical signals to a receptor, e.g. pH can be a pH-electrode, an oxygen electrode, or a piezoelectric crystal to measure the target analyte without using reagents.

(c) Transducer: responsible for transforming chemical or biological energy into useful analytical signal.

(d) Electrochemical sensor: responsible for transforming the effect of the electrochemical interaction analyte electrode into useful signal.

(e) Electrical chemical sensor: responsible for measuring the change in electrical properties caused by the interaction of the analyte.

(f) Thermometric chemical sensors: responsible for measuring the heat effects of a specific chemical reaction or absorption which is involved in an analyte (g) Optical chemical sensor: responsible for transforming changes of optical phenomena as a result of an interaction of the analyte with the receptor part.

(h) Magnetic chemical sensors: responsible for the change of paramagnetic properties of the gas being analyzed.

(i) Mass sensitive sensor: responsible for transforming the mass change at a specially modified surface into a change of a property of the support material. The mass change is caused by absorption of mass of the analyte at the oscillator.

(j) Photo-ionization detector: detects unknown organic gases and vapors and also determines their concentration level.

(k) APD 2000: detects the presence and relative concentrations of military chemical agents, e.g. satin, mustard gases, cesium (l) Bioassay strips: determines the presence of some biological agents and send results to an optical reader in the receptor to evaluate the test strip.

(m) RFID chip, a nano-structured processor for detection of weapons of mass destruction, detection of functional inability of personnel, and also for wirelessly networking with stations or fiber towers.

The applicant also acknowledges that the design of the outfit or jacket for detection requires any of five design techniques:

Piezoelectric thin film coating through pattern recognition technique.

Cantilever beam deflection technique.

Piezoelectric AlN Thin films sensors

Infrared reflectometry technique

Micro electro-mechanical system with RFID chip.

The advancement of the security sensing jacket in H-LIST calls for biological sensing elements which would selectively recognize a particular biological molecule through a reaction specific adsorption, or other physical or chemical processes, allowing the transducers to convert the result of its recognition into a usable signal, which can be quantified and amplified. Typical transducers to be employed in this invention for the detection of deadly gases and explosives in homeland security protection consist of optical, electro-optical, or electrochemical devices to enable many sensing opportunities and tailor biosensors for specific applications such as Homeland Intelligence Systems Technology "H-LIST." A typical detector such as a transducer will translate physical or chemical change within an area by recognizing an analyte and relaying its analysis through electrical signal communication from the wired/wireless connections to the embedded sensors disposed in the outfit or jacket insulators, enabling a detection platform, which may be detachable, and in connection with the receptors input for enabling communication to centralized stations.

The process of detecting biological or chemical gases involves binding of chemical species with another chemical species, which has a complementary structure, H-LIST focuses on two classes that have the bio-recognition processes for detection. These classes are bio-affinity recognition and bio-metabolic recognition and offer different methods of detection. Bio-affinity recognition has stronger binding and enables the transducer to detect the presence of the bound receptor—analyte pair and enable communication thereof. However, with the receptor-ligand and antibody-antigen bind, the processes are common to the detection environment.

The pattern recognition technique uses different recognition, such as metabolic recognition, where the analyte and other co-reactants are chemically altered to form the product molecules and communication thereof. The biomaterials that can be recognized by the bio-recognition elements are as varied as the different reactants that occur in biological system's detection in which analyte molecule will have a complementary structure to the antibody while the bound pair will be in a lower energy state than the two separate molecules, making it very difficult to break. Homeland security protection in H-LIST enables interaction between antibodies with their corresponding antigen, allowing an antibody based chemical and biosensors like immunosensors. When the antibody is raised against an analyte, an immunosensors would enable its recognition. The specificity and affinity of antibodies towards complementary ligand molecules prevents most antibody antigen interactions from causing any electronically measurable change. However, a piezoelectric effect in various crystalline substances would allow detection of analyte within that vicinity.

Piezoelectric immunosensors would detect antigens both in gaseous phase and liquid phase. Piezoelectric could also be used to detect micro-bacteria antigen in biological fluids and is incorporated in the design of H-LIST, a wearable and portable device to allowing detection of gases and explosives in any environment. Devices to detect weapons of mass destruction have been previously used in the art but all failed to teach a portable and wireless system with sensors wired in an outfit for detection and communication. Example of such device is described in U.S. Pat. No. 4,866,439 and discloses an explosive detection system for aircrafts to deter terrorist activities. This system fails to show a portable and mobile system needed for homeland security. U.S. Pat. No. 5,465,607 teaches an explosive detection screening system for detection of explosives and other controlled substances. This system shows detection of relatively volatile and non-volatile vapors and particulates but did not teach a wired outfit detection device. U.S. Pat. No. 3,718,918 teaches detection of nuclear explosion through radiated transient radio frequency signal and still fails in its teaching to show a wired outfit system that enables communication to at least a network when detection is eminent.

U.S. Pat. No. 6,573,107 teaches immunochemical detection of explosive substance in the gas phase through surface plasmon resonance spectroscopy. Still, the system fails to reach a portable, mobile and communicative system wired in an outfit to enable network interface. U.S. Pat. No. 6,569,630 teaches a method and composition for aptamers against anthrax. This system relates to detection of biological agents using different compositions and still fails in its entirety to teach a wired outfit for biological and chemical agent detection in their mobile environment. All the above references cited, whether taken in singularly on in any combination, failed to teach a wired outfit design for detection of weapons of mass destruction in anticipation of terrorism. Therefore, all objects of the present invention as listed in its entire specification falls within the scope of all its claimed entities.

SUMMARY OF THE INVENTION

H-LIST uses the most frequently used detector crystal in alpha quartz, which is suitable for piezoelectric applications in the incorporation of a silicon-micro-fibered material with embedded sensors for detections because it is insoluble in water and have better resistance to high temperatures and electrical properties which enables the transformation of electronic detection system in homeland security. The resonant frequency of the quartz crystal depends on the physical dimension of the quartz plate and the thickness of the electrode deposited. These crystals are in the form of a disc, square, or rectangle in their design. The piezoelectric quartz crystal is driven by a low frequency transistor oscillator in the receptor and is powered by a direct current regulator power supply. The crystals, which could be mounted on a holder with a stainless steel with leads embedded inside the silicon, is etched on the micro-fibered material, and then connected to the receptor oscillator circuit with the frequency counter connected to the oscillator device of the receptor. Silver composite may be used to connect the electrode to the connecting wires, thereby enabling the crystal electrodes to be modified with a 5 ml coating of protein A, and provide better adhesion of the antibodies to the surface of the transducer. Protein A, which is a polypeptide isolated from staphylococcus aurues, will bind specifically to the immunoglobulin molecules in the sensor sensitivity and selectivity process for trained specific recognition.

The applicant acknowledges that different techniques may be employed in transforming biochemical sensors, such as infrared reflectometry to characterize the thickness, and employ optical properties of thin films that are used to enable the advancement of the integrated circuit for the Homeland Intelligence Systems Technology "H-LIST," while enabling smaller feature sizes, faster switching speeds, lower power consumption, and further enabling the materials employed in the basic wiring such as dielectric and photolithographic layers to change dramatically. This integrated circuit could employ copper/low-k interconnects, silicon-germanium and silicon on insulator-based transistor structures, or chemically amplified deep ultraviolet and x-ray lithography and new metal silicide ohmic contact materials in its process. Infrared spectroscopy offers a metrology approach to sensing through the outfit, complementary to UV-VIS techniques, that provide excellent sensitivity to layer composition, including chemical bond densities and free carriers with the enhanced immunity to roughness induced scattering. Infrared spectroscopy shares many of the inherent advantages of UV-VIS spectroscopy as a non-destructive process control tool for future usage in H-LIST because it can be implemented as a reflectance sensor embedded within the outfit. A reflectance spectrum is acquired by using a sysetm incorporating a reflectometer equipped with a linearized liquid nitrogen detector. Software is also incorporated to analyze input to the model-based.

The dielectric function of the layer is modeled with a basis set of damped harmonic oscillators closely spaced in frequency, with equal damping constants and spacing. The arrays of oscillators are located in the spectral regions where absorption is expected in the film. During the fit, the amplitudes of the oscillators, high frequency dielectric constant, and layer thickness are varied to fit the model to the measured data. By combining model-based infrared spectral analysis with high performance reflectometry hardware, it is possible to extract quantitative data on multiple parameters related to film properties. These have a unique sensitivity to film composition, which is applicable to a wide range of films including ultrathin oxides, doped semiconductors, and complex materials such as photoresists and low-k dielectrics. The high accuracy reflectometer characterizes the reflectance of ultrathin gate oxides and chemically amplified deep ultraviolet photoresist thin films. The gate oxide reflectance data is related to the deposition time needed to model the thermal oxidation growth kinetics. The H-LIST set goal is to employ non-destructive measurements on every product wafer as a means of gathering data and information needed to control the process of monitoring biological or chemical gases or weapons of mass destruction in a confined environment. Ultraviolet visible reflectometry and ellipsometry could also be employed in the outfit detection with other widely accepted method for production monitoring of transparent thin films.

BRIEF DESCRIPTION OF THE DRAWINGS

In order that the invention may be readily carried into effect, it will now be described with reference to the accompanying drawings, wherein:

FIG. 1 is seen to represent a piezoelectric quartz and receptor transducer on a sensored jacket connected to a receptor.

FIG. 10 is seen to represent various networks

FIG. 11 is seen to represent a stationary wind tunnel, command post, and wind stations for enabling communications.

FIG. 13 is seen to represent security officers with their outfit worn and monitoring a street and the government building on the said street.

FIG. 14 is seen to represent the different possible combinations of outfit design for monitoring means.

DETAILED DESCRIPTION OF THE INVENTION

Figure 1:
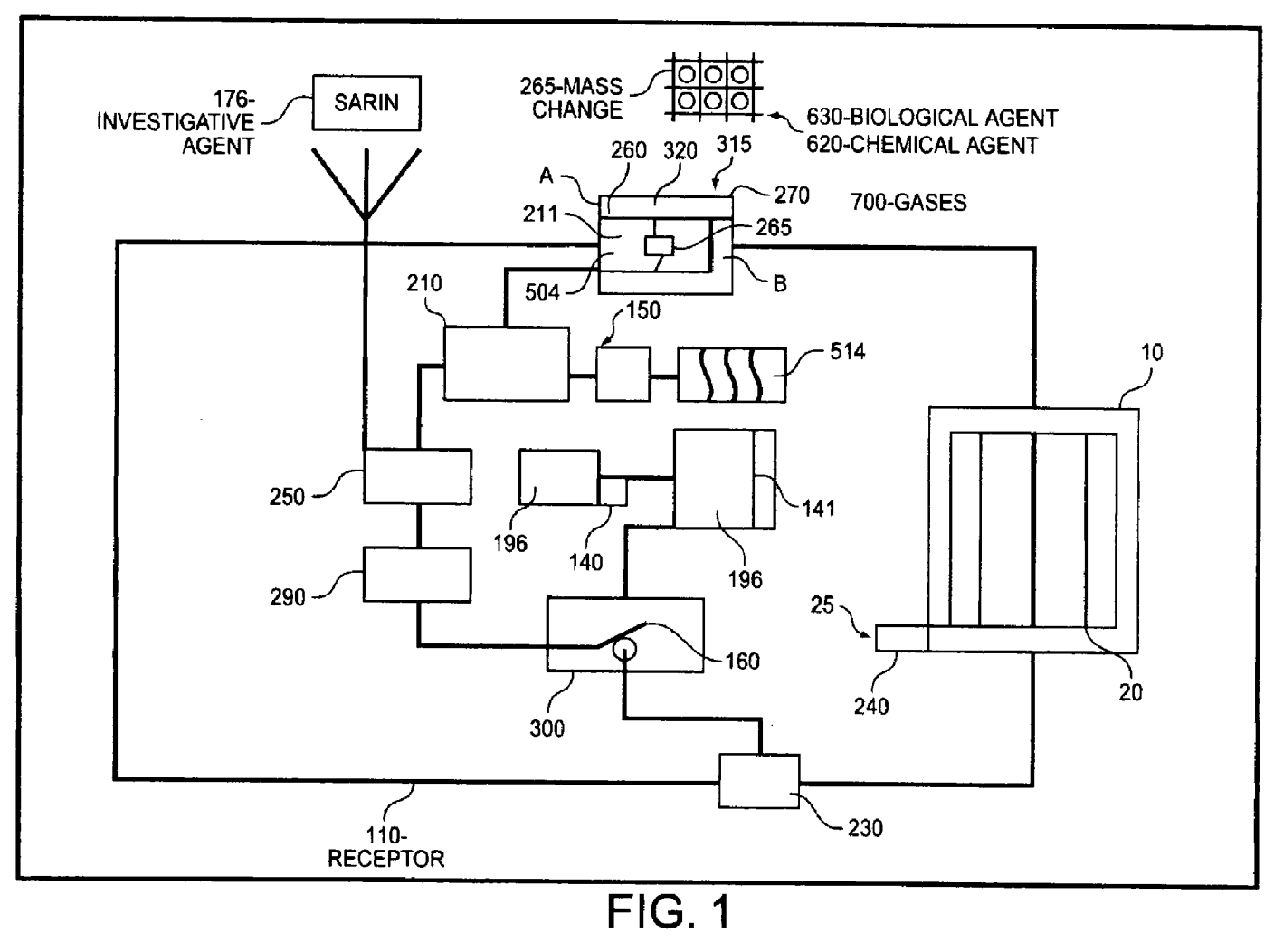
Figure 2:
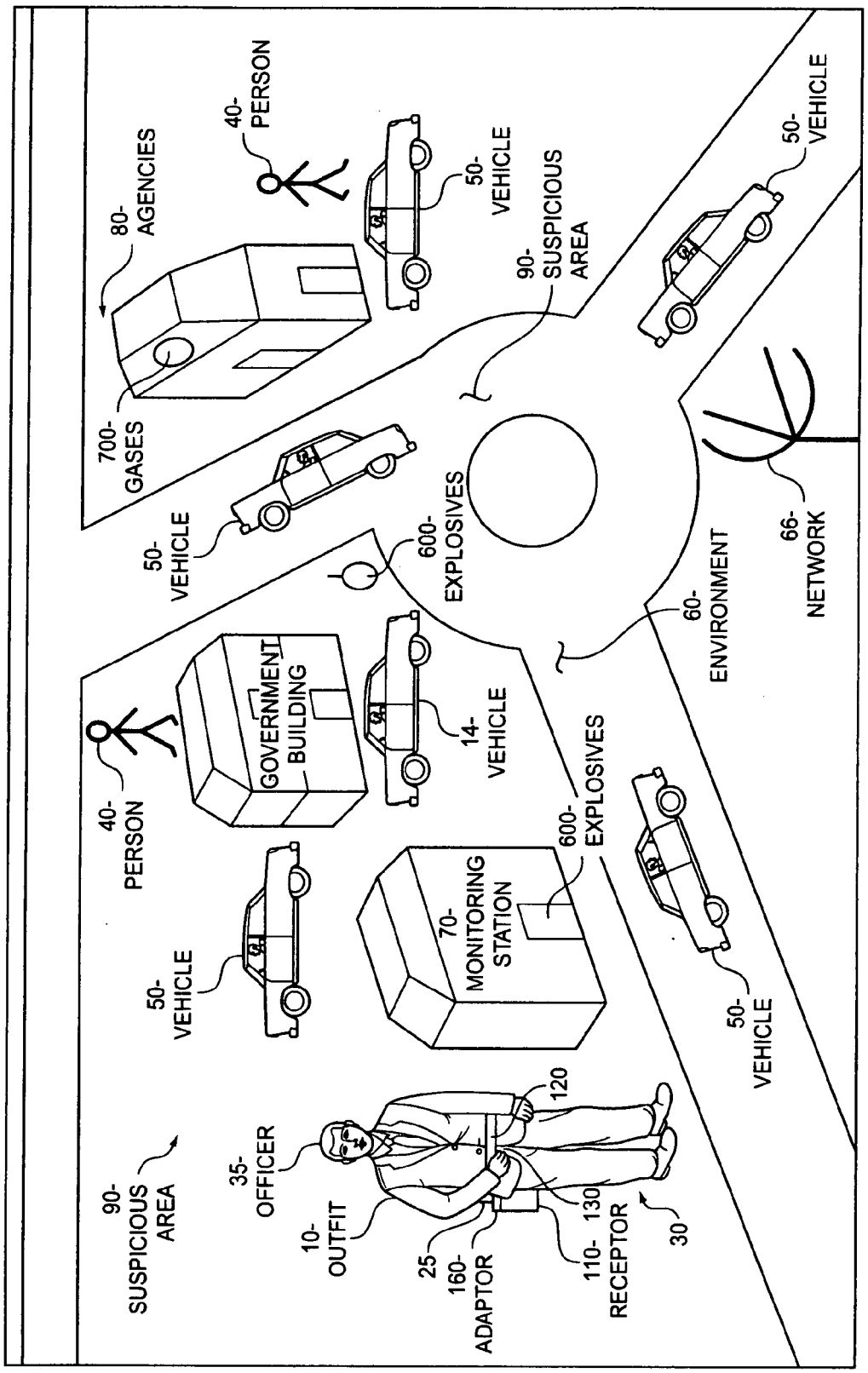
FIG. 2 is seen to represent an officer randomly patrolling an environment.

The present invention introduces Homeland Intelligence Systems Technology "H-LIST," an advanced system's jacket (10) or outfit that is worn by officers, security officers, TSA officers, FBI, CIA, custom officers, boarder patrol officers, military officers and the like, to enable detection of deadly gases (700), and explosives (600), or any weapons of mass destructions, analyzing information and transporting the analyzed information wirelessly through waves to a central security monitoring station (70) or networks, to speedily prevent any use of such weapons, or advice occupants to stay clear from such environment (60) where one of such weapons such as gases (700), had been used. FIG. 1 is seen to show a piezoelectric device with a piezoelectric crystal (260), which allows antibodies (270) to be coated with the crystals to enable multiple use potentials in a solid, liquid, gaseous and explosive detections in all environment, including military, customs, CIA, FBI, chemical firms, biological firms, radioactive firms, healthcare, hospital facilities, commercial industries monitoring and healthcare monitoring, transit buses, buses and transit trains, airports, nuclear power plants and the like. A piezoelectric device incorporates an immunologically active sensing element in the outfit (10a) with electronic transducer (315), for sensing antigen/antibody concentrations by direct changes in the transducer output (317) and converts immunoreaction activities into different physical signals.

The antigen/antibody affinity reactions are identified directly by measuring the frequency change of an environment, which corresponds to a mass change of the sensor surface. The present invention is designed with high sensitivity and lowers power supply automation to specific detection of deadly weapons. The invention consists of antibody coated piezoelectric quartz crystal transducer (315) and signal-processing systems, causing coated crystals (A) to selectively vibrate at fundamental harmonic frequencies. The coating traps particulates that change the effective mass (265) on the sensing surface that enables a change in oscillating frequency of the antibody-coated crystal (A). A change in the oscillation enables signal communication, reaching central security monitoring stations (70) and other agencies (80) or networks while also identifying the chemical and biological mass that has been detected based on the impacted crystal or specifically on the coated region of the recogrution pattern. The device particularly employs transducer (315) for detection and integrates with the piezoelectric crystal technology.

Figure 6:
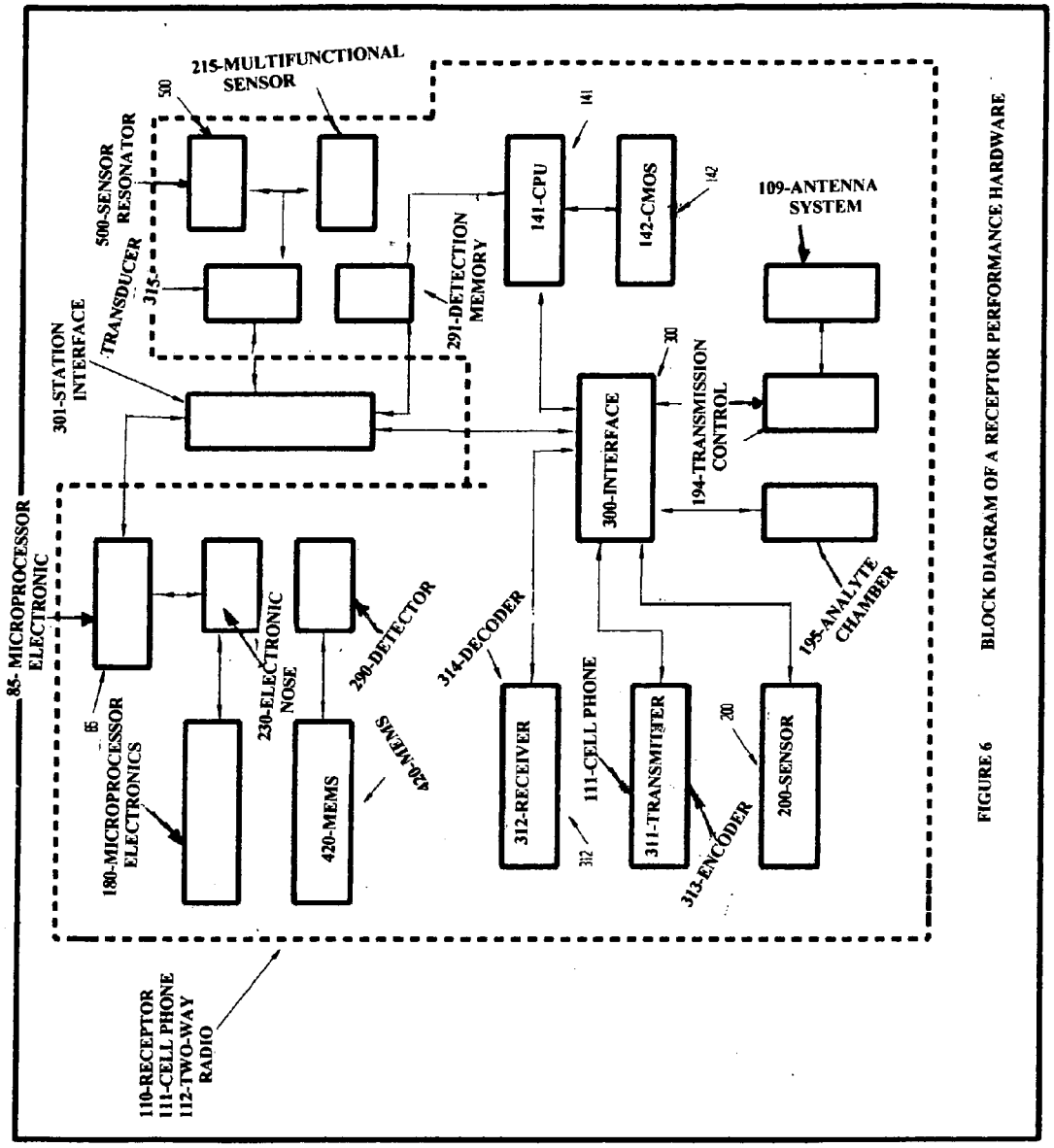
FIG. 6 is seen to represent a block diagram of key components of receptor performance hardware.
Figure 7:
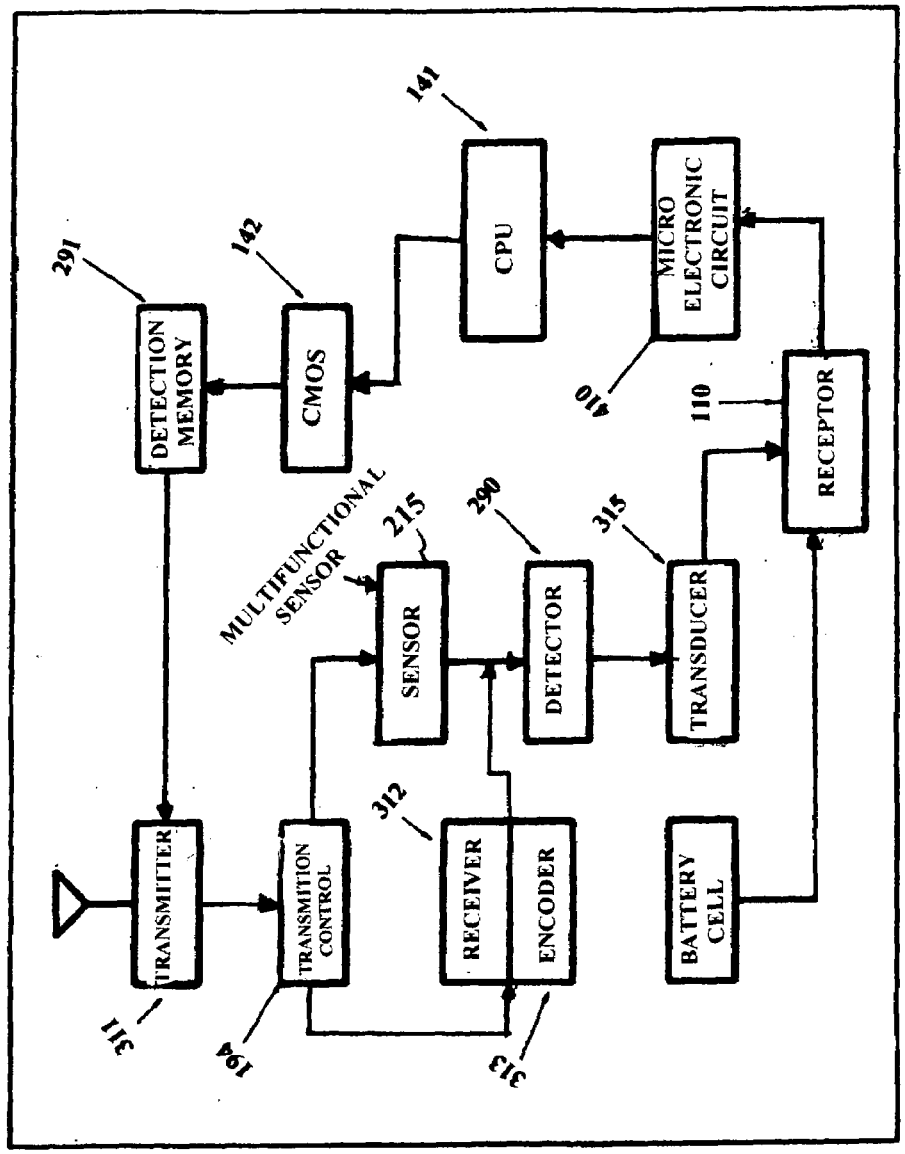
FIG. 7 is seen to represent a detection array of the detection system.
Figure 8:
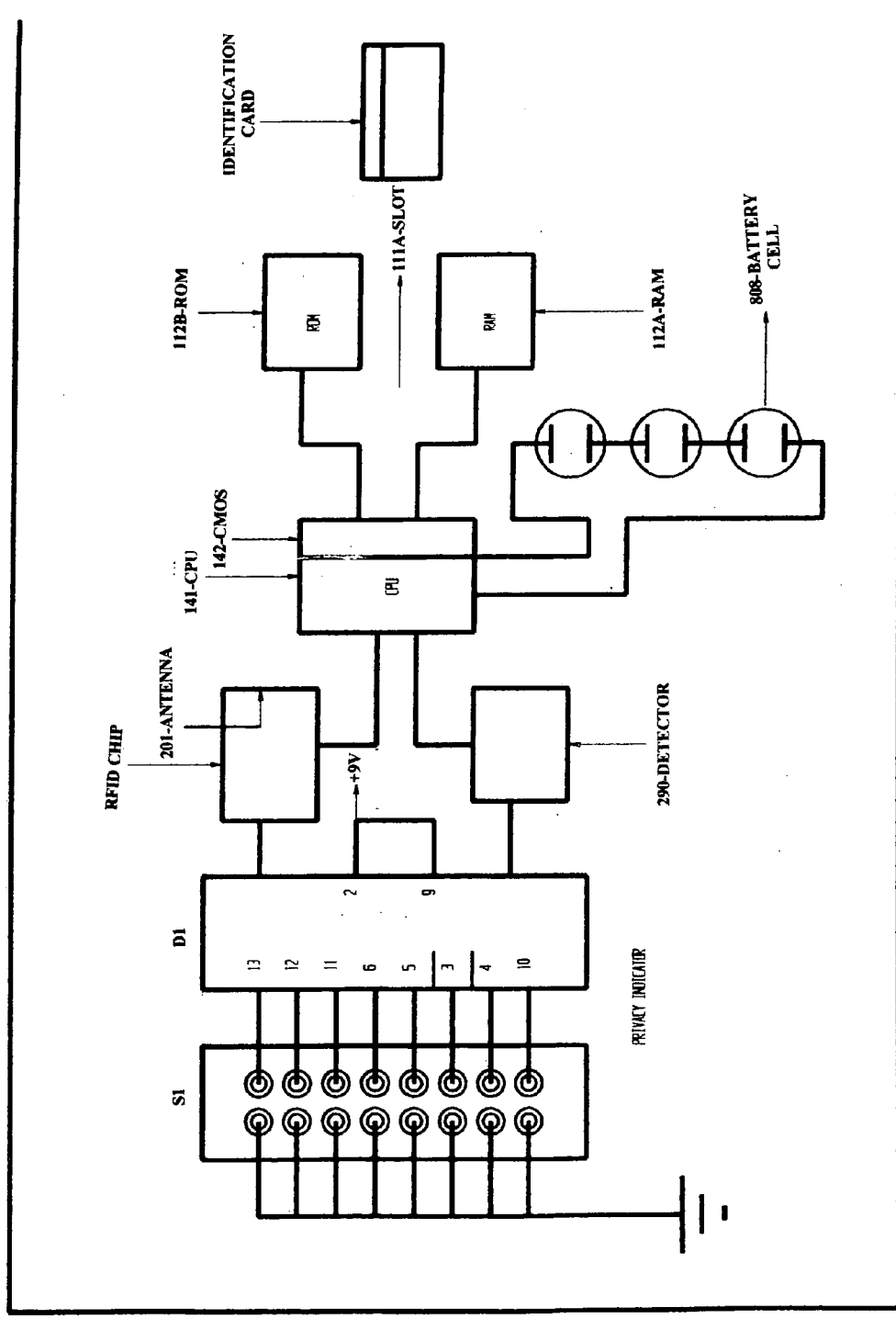
FIG. 8 is seen to represent a circuit diagram for the receptor privacy indicator with silicon battery cells.
Figure 9:
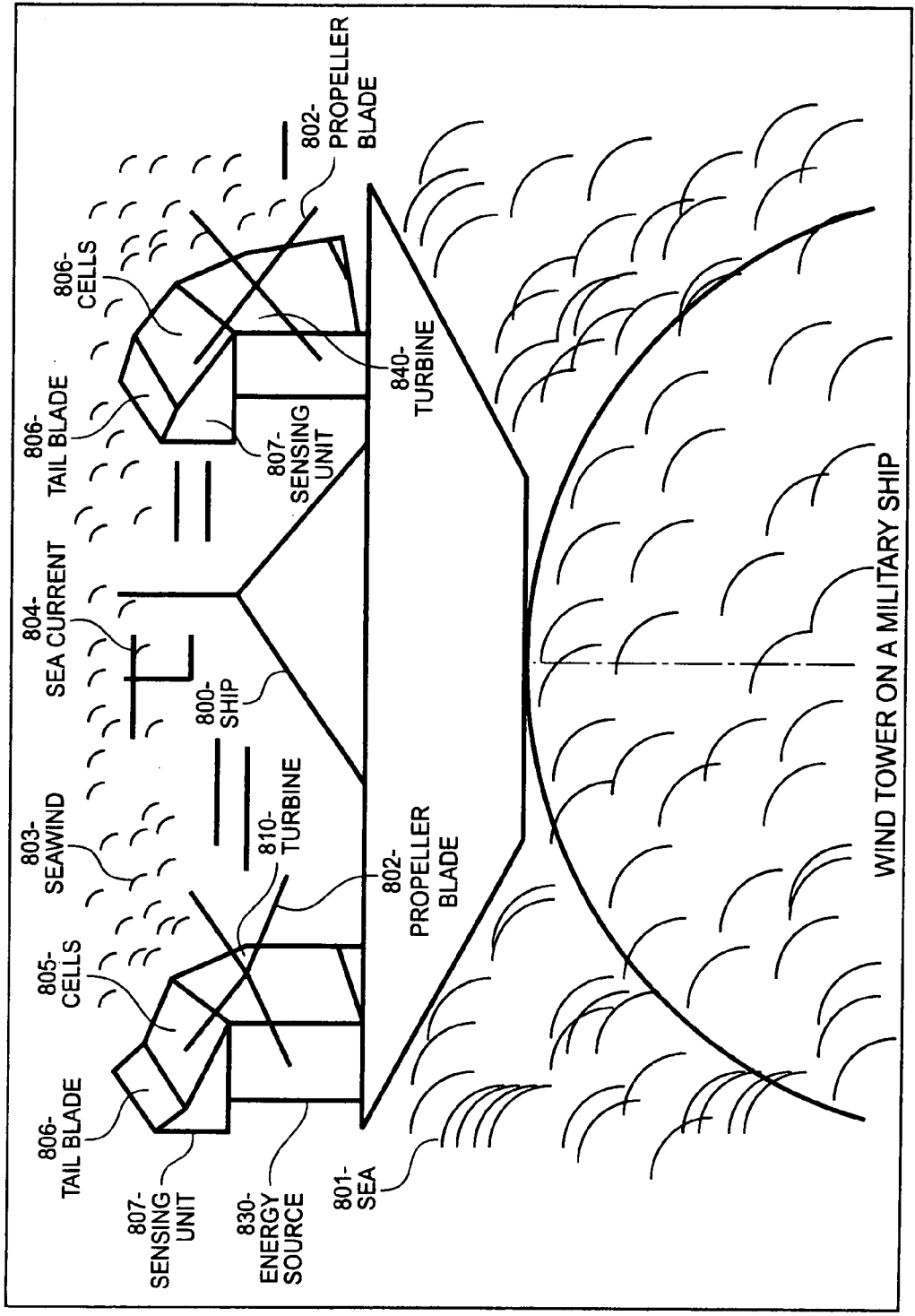
FIG. 9 is seen to represent a sailing military ship with wind towers for empowering military outfits and receptors.

Antibodies (270) are coated on the crystals of the piezoelectric (180) at specific harmonic nodal positions to enable a change in mass that will cause a change in the frequency of the associated harmonic. That is, a change in mass (265) changes harmonic frequencies of the detection material. FIG. 6 further shows a functional block diagram of the receptor (110) with sensors (200) for further detection of the presence of particular biological and chemical explosives, and enables detection of oscillating frequencies of two crystals due to their absolute frequency shift. A transmitter (311) generates radio frequency signals and sends detected signals to a frequency-modulating receiver (312). The FM receiver (312) receives signals from the radio frequency identification "RFID" chip (200a) through the chip's antenna (201), decodes the signals, and informs the central security monitoring station (70) of the sensed agent based on the pattern recognition of the foreign wave in the radio wave frequencies and the like. The sensors (200) or (200a) and decoder (314) are connected to a detection memory (291) for repetitive signaling, and the encoder (313) and the transmission control (194) are connected to an analyte chamber (195), while the frequency transmitter (311) is connected to the encoder and the transmission control (194) to enable real time interactive control means, detection means, and reporting means to fiber towers or networks (69).

The transmission control (194) provides information about detected agent's status to avoid false recognition of the said agent due to unidirectional pressure effect on the wave's path. Signals are coded and sent to and from the transmitter (311) to the FM receiver (312). The transmitter (311) transmits continuous and repetitive coded signals until they are received by the central security monitoring station (70) or network (69). The sensors (200) or (200a), transmitter (311), detector (290), and the FM receiver (312) are the basis of the wireless communication for homeland security monitoring and enable uniformed army personnel or officers (35) to monitor the deployment of deadly agents and the detection of other weapons of mass destruction within a defined environment. The officers (35) will wear uniform jacket (10) or other outfit (10a) which is electronically etched with plurality sensors (200) or (200a), and the officers (35) will be assigned to a detection zone, battlefield, or environment (60) for monitoring. The detection of anticipatory suspicious person carrying deadly gas (700) or explosives (600) will not only produce limited visual or audio signal, but rather inform the officer (35) through other means, such as vibration, while wirelessly communicating to central security monitoring station (70), wind fiber towers (71), or at least a network (69). H-LIST uses radio frequencies means on its RFID chip (200a) or receptor (110) to receive and transmit sensed data, which allows the use of cell phones (111) and two-way radios (112) connection as auxiliary receptors to further add protection in the homeland security monitoring. In some embodiment, sensor (200) is seen to represent at least an RFID chip (200a) in the size of at least a human hair.

The chip (200a) is embedded in a silicon substrate (205) and etched in a micro-fibered material 220), for enabling tracking of communication between terrorist networks and the like, and for enabling interactive communication between the system for the instant invention and enabling communication thereof with digital network facilities within homeland security agencies and the military; and for detection of weapons of mass destruction such that antenna (201) is etched in the chip (200a) and faced outward to track foreign objects traveling through wind waves. The chip (200a) is embedded in a silicon substrate while the antenna (201) is embedded in the chip (200a). The embedded chip (200a) with the antenna (201) all embedded in the silicon substrate (205) is then etched in a micro-fibered material (220) for future use as a fabric material for an outfit (10a) designed to enable digital wireless network and mobile detection of weapons of mass destruction. In another embodiment, the micro-fabric material (220) is used for the design of innovative military outfit with chip (200a) coded to detect enemy personnel and persons, such as a terrorist carrying at least a weapon (600), or a guerilla fighter in his hidings, such that all detections are communicated to networks (69) or command post (70) or (71).

The outfit (10a) is designed to receive input signals and to send out output signals through its embedded antenna (201), for gathering data (such as that of a fallen soldier and his pulse rate) and equally sends communication indicative of whether or not a staff is alive. The system monitors heart beat and respiratory system; and communication to at least a network is enabled if the heart stops beating or the respiratory system under goes a drastic change. H-LIST enables modernizing homeland security and battlefield personnel on digital combat against any act of terrorism and/or guerilla style attack, wherein all field communications are connected to a common network (69), (70) and (71). A typical example of a common network (69) is at least, the equipment used in a battlefield, that which are used to attack enemies or monitor enemy movements, wherein detection and communication to battlefield personnel is enabled through the instant invention. By networking homeland personnel and/or army personnel, whether independently or collectively, allows a cohesive integration and collaboration through wirelessly sharing of field data to enable real time responses and devastating force of action towards weakening enemy lines. In a similar example of a typical network, the embedded antenna (201) in the RFID chip (200a) or sensor (200) is seen in the instant invention operating as a retractable device that reads information traveling through waves, such as radio waves or micro-waves, and communicating such information wirelessly to command post computers or at least a common network station computers for analysis and instructions.

When the outfit (10a) of the instant invention is amplified, the chip (200a) will emit beams through the antenna means (201), invisible beams that will travel through waves, such as radio waves, micro-waves, ultrasonic waves and the like. Each emitting wave will carry certain current and will travel through a trained pattern to read information that will enable locating the exact location of weapons of mass destruction, or activities in anticipation of creating such weapons of mass destruction, or location of enemy personnel. A typical chip for the application of the instant invention is a radio frequency identification chip (200a) "RFID CHIP" with the embedded antenna (201), wherein both the chip (200a) and the embedded antenna (201) are further embedded in a silicon substrate (205) and then etched in a micro-fibered material (220).

The micro-fibered material (220), which is made of a non-ferrous material such as at least silver micro-fibers, innovatively re-enforces the fabric and enables a wired outfit (10a). It is anticipated that the incorporation of a non ferrous micro-fibered material (220) within the fabric for the outfit (10a) and the RFID chip (200a), or silver micro-fiber in particular, will allow the electrical properties of the material used to respond to temperature conditions and also respond to bacterial in human bodies created by the environmental condition of the site, such as biological (630) or chemical agents (620) in the air. Such that, in a real severe environmental weather condition, the electrical properties of the silver micro-fiber (220) will reverse or bias the situation, enabling the system to thermostatically operate partly as an HVAC control system's outfit (10a), partly as an outfit (10a) designed for anti-bacterial device that fights biological and chemical agents that could possibly come in contact with the skin of a personnel wearing the said outfit (10), and largely as a protective and monitoring outfit (10a) device for the detection of weapons of mass destruction and also for tracking heart beats and respiratory systems of army personnel, wherein communication is enabled when any of such detection is sensed. Once the chip (200a) encounters any detection, wireless communication means is enabled through a receptor (110) that will amplify the communication signals or means to a network (69) of security agents or military personnel. Such network (69) includes wind towers (71) for tracking down other terrorist activities and interactively communicating with personnel wearing the outfit (10a) of the instant invention at their assigned locations.

The receptor (110) has an insertion slot (111a) to be used by homeland security agents, such that trained personnel would request an identification card (112) such as a driver's license from a real suspect in anticipation of an attack and insert the ID card (112) in the slot (111a). Inserting the driver's license into the slot (111a) of the receptor (110) will enable the ROM (112b) to read the ID card (112) and communicate to the RAM (112a) to access the database (113) where such ID information is stored for retrieval, while a screen read-out (113a) on the receptor will enable full information about the anticipatory suspect retrieved from at least a database (113) of driver's licenses. An 8-pin privacy indicator (S1) enables the receptor to communicate to an officer in private when a weapon is sensed. The indicator has switch S1 as the display selector and correspond to cathode a, cathode g, and cathode d of a 7-segment common anode display settings (D1). The chip (200a) acts as a detection tool and would enable intranet communication means within global homeland security agencies or the military, making it very possible for agencies to identify treats or any object of terrorist attack or enemies at battle fields.

The RFID chip (200a) could be coded to identify members of the agencies such as battlefield personnel and other security personnel, and distinguish the said personnel form enemies at battle front or terrorist personnel. When the chip (200a) is coded, the system will provide means to feed trained security personnel and military personnel with reliable, accurate, and real time information about anticipatory act of terrorism or any mobility of enemy personnel in a battle field, an innovative approach of combating any war. The technical characteristics of the RFID chip (200a) provide opportunity for innovation in the war of terrorism and any other war thereon. The outfit (10a) with the embedded RFID chip (200a) or the sensors of the instant invention will enable airport personnel wearing the said outfit (10a) of the instant invention to be pro-active in their assignments in that, the system will read off information in a wallet, pocket book, or luggage and single out any one of such luggage if detected or suspected of any weapon for extra checks, enabling a vision possible in H-LIST. That is, the fabric material used for outfits or jacket insulation is replaced with the technology of the instant invention to enable wireless and mobile detection of weapons of mass destruction, such that the chip (200a) is etched in at least a silver micro-fibered material (220) to enable conduction of body heat and further as anti-bacterial means.

In another embodiment, the chip (200a) is etched in a battery-powered fabric (220a) that empowers the sensors embedded in the fabric to amplify detection pattern of weapons of mass destruction. The selective recommendation of a silver micro-fiber (220) is to enable its many natural properties, such as its anti-microbial and its ability to eliminate static electricity by dissipating the static electric charges. Additionally, its thermal conductivity property would enable innovative homeland security technologies. The chip (200a), which is a processor means, includes a pattern recognition technique for producing "Sensing," a controlled communication signal and communicates any sensed detection to a wireless modem or control module that in turn controls communication wirelessly to security monitoring agencies or network (69) so as to optimize the protection against terrorism and hence monitor the mobile capabilities to assigned terrorist locations.

The system accepts input from security agents, security agencies, security stations, and guards in anticipation of a terrorist act, such as suicide bombing. When such detection is eminent, the system for the present invention will involve wind pattern towers to reach other agencies for immediate reaction. The pattern recognition technique in this invention processes signals that are generated by objects and the said signals are periodically modified by interacting with other objects in order to determine which of the classes the objects belong to—radioactive, biological, chemical, and explosives. The system as introduced in this invention generates signals based on the detection of at least a class of the object. The system then determines if the object is of a specified class and then assigns the object to the specified class code, or sends out other signal if the object is not a member of any of the coded classes in the set. The signals thus generated are electrical and emanates from at least a transducer (315). They are shown to be very sensitive to radiation from weapons of mass destruction. The instant invention enables anticipatory sensing pattern recognition technique and further enables communication to network (69) in anticipation of terrorist activities. Such anticipatory sensing is hereby described in the instant invention as Homeland Intelligence Systems Technology-LIST."

In other embodiment, the sensor (200) or (200a) is etched in a silver fibered material (220) to form a bimetallic layer to enable antibodies of chemicals and bio-molecules for detection of high explosive substances in their solid, gaseous, and liquid phases. The bimetallic layer is mixed with other substances at different points of their embodiment to enable highly specified detection of terrorism device applications. Such mixtures suggest micro-layers of surface plasmon resonance spectroscope on the surface of the sensor (200) and (200a) and then etch the combination on a silver micro-fibered material (220) to enable highly sensitive detection device for anti-terrorism application. These teaching combinations are highly reliable for security monitoring and for detection of weapons of mass destruction, which requires portable, mobile and wireless networks (69), wind station networks, satellite networks and the like. This innovative approach to security and monitoring means includes all as military, Government, law enforcement, hospitals, industries, recreational facilities, sporting events and facilities, amusement facilities and the like. After the combination has been etched on a silver micro-fibered material (220), and later used for the design of an outfit (10a), the outfit (10a) is then connected to a receptor (110) through a ribbon output terminal to the input slot (111a) of the receptor (110).

The receptor (110) then empowers the outfit (10a) to enable high specificity and low detection levels for the design application of security and monitoring, and the detection of weapons of mass destruction. In introducing portable, mobile and wireless detection and communication system, the receptor (110) will enable amplification of the sensors (200) and (200a) and all the other embedded sensors to allow speedy detection within a mobile environment. This innovative method of detection as prescribed in the present invention is simple in its application and very specific in its detection. Its wireless communication means to network stations provides convenience to use. The receptor (110) is very specific in its analysis and it is self-diagnostic. The receptor (110) also enables detection of contraband substances within a container or luggage. Its CPU (141) enables interface means between the sensors on the outfit (10a), the receptor (110), and the network stations to enable interactive communication thereof when detection is eminent. Detection of vapors emanating from explosive substances and weapons of mass destruction is timely, such that when a particulate matter is emitted from its substance, its concentration or presence will immediately be detected and communication is then enabled from the detection environment to the network stations (69), which are classified and/or unclassified for security monitoring of at least a nation.

The receptor (110), which functions both as an amplification device and also as a control system, controls and processes the overall detection instantly and enables wireless communication to at least a network station. The detection process enables constant monitoring and requires no tunnel for people to walk through, but rather detects these people as they walk pass a person wearing the said outfit (10a). Its mobile detection means is portal and invasive, preventing any act of suicide bombing or other acts of terrorism while also enabling a non invasive detection means when the particulates in the wind waves are non destructive. The detection of explosives or contraband emission is from concealed substances on individuals, luggage, vehicles, trashcans, airplanes, buildings, and other areas where such weapons could be used. Because many particulates of substances can be contained in wind waves, the sensors on the outfit (10a) are outlined and configured to single out each concentration of various particulates that may be sensed or detected within terrorist networks, enabling effective sensitivity and reliability to its detection of absolute solution for critical analysis of weapons of mass destruction.

The silver micro-fibered material (220) also serves as a filter element sensing medium to absorb particulates for analysis in their mobile environment, while the antenna (201) also provide a thermal means to vaporize and evaporate the particulates to increase selectivity and sensitivity for detection, and thermostatically provides HVAC means in response to other environmental conditions to burst reliability under all weather conditions. The central security monitoring station (70) is linked to the receipt (110), which enables communication with various stations through the radio frequency signals generated by the transmitter (311). A microprocessor (140) is connected to memory (291) through input and output interface (300) to the analyte chamber (195). The receptor (110) includes an antenna system (109) for receiving radio frequency signals from the sensors (200) and/or (200a), which are empowered by the transmitter (311). The receiver (312) and signal decoder (314) processes signal, the decoded signals are then transmitted through interface (300) and (301) to the central security monitoring station (70) or network (69) and other agencies (80). The receptor interface (300), and the central security monitoring station interface (301), wind towers (71), or other networks such as megatel (3001), vehicles (14), computers (11), base stations (13), branch stations (16), highway advertisement board (007), industries, police stations, and schools are connected through wireless links or modem to the radio frequency or infrared links.

The receptor powers the outfit (10) through a fiber optic ribbon (240) or wireless connection means (241). The wireless connector (241) includes a transmitter (242) and a receiver (243) and need at least a 9 Volt power for its initial energy from the silicon battery cell (808). The silicon battery cell (808) is the central energy source and empowers the amplifier to enable active emission of beams over the sensing surfaces of the outfit (10). Because the sensitivity of the wireless connection depends on the light in the environment, the transmission and reception quality is then enhanced by shielding the IR LED and the phototransistor by focusing the IR beam with lenses. The potentiometer is adjustable to get the best possible connection signal. The wireless connection is a secondary connection means when the fiber optic ribbon or cable connection becomes faulty. The wireless connection uses infrared transmitter and receiver to carry energy to the sensing medium. Since the wireless connection is a secondary means, more emphasis is on the ribbon connecting means. With the fiber optic ribbon connecting means, a more timely sequence of events is preprogrammed, so that when any of the sensors senses weapons of mass destruction, plurality reaction is enabled through the receptor's random analyzing circuit (244), to enable a random output through the receptor (110).

A LED is fired each time the sensors (200) or RFID chip (200a) sends a pulse or signal. The pulse rate of emission is adjustable through the potentiometer to enable flexibility for random adaptability to other sensing environment. One lead of the LED represents the anode and the other is a cathode. All the anodes may be connected to the resistors R3. A pulse from any of the sensors enables contact at switch S1, which will then able connections to networks and other security institutions. When S1 is broken, at least one of the LED will stay lighted to indicate active power in the IR system and can be adjusted to higher clock speed. The transmitter accepts signals from the sensors in the outfit (10), modifies the signals and carries the signals through waves or beams to the satellite or network stations "Receiver." The beams, which are of infrared light, are translated at the receiving end back into signals that can be easily amplified to understandable or readable information and communication data. Reply from the receiver is obtained through the receiving circuitry of the receptor (110).

For a military combat setting, a military advanced combat system's technology employs a battle ship (800) with wind tower (71) positioned in the sea (801). The wind tower (71) has propeller blades (802) aeronautically powered by natures sea wind (803). The wind tower (71) has a tail-vane (806) that enables the tower to rotate with the wind, creating a kinetic energy along its movement. The kinetic energy of the movement of the wind (803) enables sea current (804), which is then stored in cells (805), for energizing the receptors (110) through the receptor's silicon battery cells (808) while in combat operations. The empowerment of the receptors (110) with the energy generated by the wind tower (71) is much powerful and will continuously energize the receptor for the entire life of the combat. Creating a night time and day light energizing means that is much stronger, powerful, and dependable than solar energy means. The receptor will utilize the natural form of electrical energy in ocean current through wind tower (71), though similar towers could be positioned around the country to empower commercial homeland security receptor devices.

The wind tower (71) includes an automatic sensing unit (807) that enables a revolving beacon light to emit constant beams of electrical energy to the receptors (110), and also empowering the military outfit (10) for unique sensing range. When a sensor (200) or (200a) senses gases or other objects, the transmitter (311) will generate a radio frequency signal-using antenna (109) through continuous wave burst with an identification code unique to the type of wave generated by biological or chemical gases and explosives. When such wave signals are matched, communication is enabled to promptly protect the vicinity where such signals were matched. The radio frequency signals are sent and received through the antenna system (109) to the frequency modulator (312) or modem. The modulator (312) outputs modulated signals to the microprocessor chip (140). The microprocessor (140) then filters out the signal output to improve signal to noise ratio and compares with the wave pattern of the coded detection agents.

The sensors (200) or (200a) operates on many different principles of detection. These principles include, but are not limited to infrared and thin-film detection, piezoelectric crystal and transducer detection, piezoelectric cantilever detection, piezoelectric MEMS detection and the like. The receptor (110) or cell phone (111), or two-way radio (112) receives output from each of these sensors and output signals indicative of the signals received. The algorithm of the techniques of the sensors sensing pattern will minimize the likelihood of any false detection of deadly agents. The output of each of the sensors and detectors are connected to the input of a central processing unit "CPU" (141) comprising a CMOS (142).

FIG. 2 is seen to describe an officer (35) wearing such outfit or jacket (10) and patrolling an environment (60), a suspicious areas (90) or between suspicious vehicles (50), allowing the jacket or outfit (10a) to detect deadly gases (700) or explosives (600) around such vehicle (50) if the said vehicle is carrying any deadly gases (700) or explosives (600). An officer (35), wearing such jacket (10) or outfit (10a) and patrolling around a suspicious person (40), allows the jackets (10) detection of explosives (600) or gases (700) if the person (40) has any of such explosives (600) in his possession.

The explosives (600) and deadly gases (700) have recognizable wavelike properties, and the sensors (200), which are embedded in the silicon substrate (205) and affixed inside a jacket (10), have trained behaviors that are recognized by the embodiment of the present invention, enabling the detected information to be transported in data form to a central security monitoring station (70) or network close to the area of detection. FIG. 6 is seen to describe a receptor (110) vibrating, ringing, or sounding an alarm when the said jacket (10) senses any weapon of mass destruction, or the detection of any weapon to activate the receptor (110), enabling wireless communication to the central security monitoring station (70) or network. The receptor (110) is coded to identify its base or location; such base could be the airport or an assigned government building each time communication is enabled to a central security monitoring station (70). The transmitted data is communicated to these stations wirelessly for urgent responses to the referenced detected situation within the vicinity of the detection and the detected device. This could be explosives (600), chemical (620), gases (700), biological (630) or other agents and the like, which are normally hidden in a transit bus, thereby requiring the transit bus drivers to wear the instant outfit (10a) of the instant invention in H-LIST. This invention advances sensors and incorporates the sensors in a designed outfit built on pattern recognition technique, discerning meaningful destructive information on materials that are mostly carried by people in anticipation of terrorist or destructive intensions, allowing significant recognizable pattern technique to enable prompt actions to the detected situation.

Figure 3:
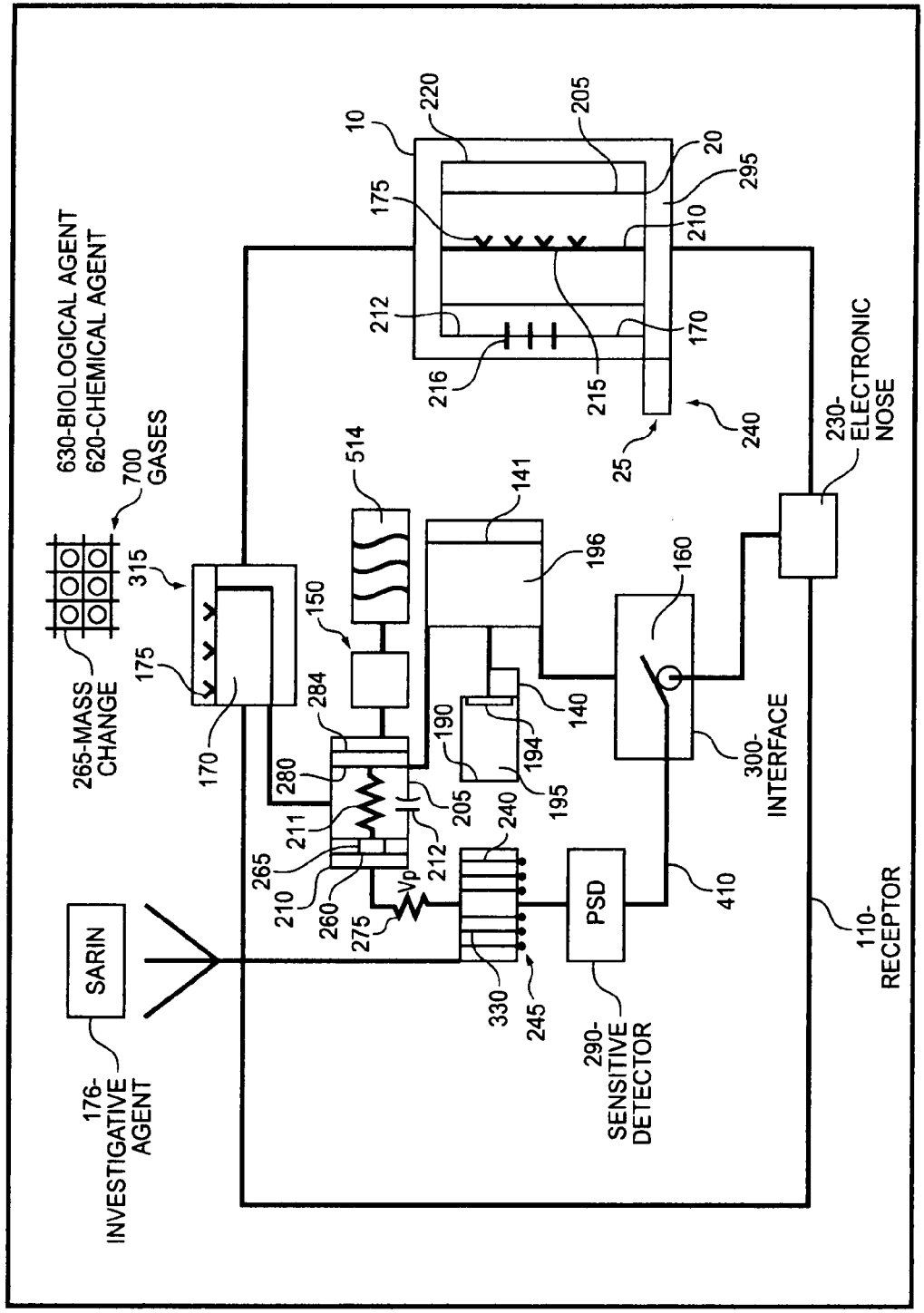
FIG. 3 is seen to represent a cantilever beam system on a sensored jacket connected to a receptor.

H-LIST detection, which is a biological, chemical, or explosive tool, enables wireless communication to receptors (110) and central security monitoring stations (70) when any or such combination, such as chemical (620) or biochemical material (640) is detected. The invention, which also is designed to facilitate the work of TSA, filters out analyzed data from an environment (60) and communicates to a portable receptor (110) and the nearest central security monitoring station (70) or network (69). FIG. 3 is seen to show H-LIST detection which allows subsequent position readout from cantilever beam deflection technique through micro-fabricated array of cantilever type sensors (210) embedded in a silicon substrate (205) and etched on a micro-fibered material (220), enabling a wearable and mobile detection of an environment (60). The cantilever (205) is coated at the side with different sensor material (212) to further enable detection of specific gases (700) or explosives (600). These sensors (600) and (700) are selectively arranged in a micro-machined etched cavities (216) on silicon substrate (205) or wafers with the rear face terminated with micro-fibered materials (220) acting as a jacket lining (20) or insulator and carries multifunctional sensors (215) that enables knowledge, and information on optical properties of the sensing gases (700) and explosive elements (600) as they as exposed to the analyte (175) carrying aqueous solutions.

H-LIST detection operates on multifunctional sensing and employs an electronic nose (230) to enable detection of different odors from its receptor layers (170) to an analyte (175). The receptor (110) has an enabling chamber (195), which is linked to the silicon substrate sensor array of the micro-fibered material (220). The silicon substrate array interfaces with the output connector (25) of the said micro-fibered fabric (220) and the input adaptor (160) of the receptor (110), to enable a more advanced selectivity and sensitivity and also to allow speedy and timely responses to multifunctional detections. The array of the cantilever (210) is micro-mechanical with multiple silicon substrate cantilevers that are linked to the analyte chamber (195) that absorbs all sensed information. Grains of membrane (190) are etched in the analyte chamber (195) to enable signal separation for specific reporting to network stations (67). The cantilevers (210) could be of a micro-machined single crystal microcantilevers with multiple resistors, with piezoresistor (211) fabricated in the cantilevers (210) for determining the cantilever stresses resulting from stress films deposition on the cantilevers (210). FIG. 3 further shows a capacitor cantilever beam (212) configured to electro-statically be pulled in into a substrate (205), to enable the pulled in voltage (Vp) to operate as a function of the dimensions of the micro-beam devices (280) and the modulus and stress state of the beams (280). The beam deflection signals are transformed into information specific to the analytical useful signal from the reaction of the analyte (175) or the physical property of the investigative agent (176). The analyzed information is then readout simultaneously through a beam deflection (284), outputting through a multifunctional fiber-optic ribbon (240) or micro electronic grains of sensors.

Multiple light sources (245) are connected through membrane (190) into the analyte chamber (195) to illuminate individual cantilever (210) with light beam through the fiber. The deflection of the light (245) from the cantilevers (210) would shine on a position sensitive detector (250), enabling bending of related sensors through photocurrent (275) due to stress factor acting on the beam (280). The photocurrent (275) is then transformed into voltage (Vp) and the voltage creates pressure on the cantilever (210), enabling bending indicative of the detected signals communication to central security monitoring station (70). The occurrence of the bending is due to surface stress on the sensors and creates resonance frequency shift (514) caused by the surface stress change, which is subsequently caused by the change of mass (265).

Figure 4:
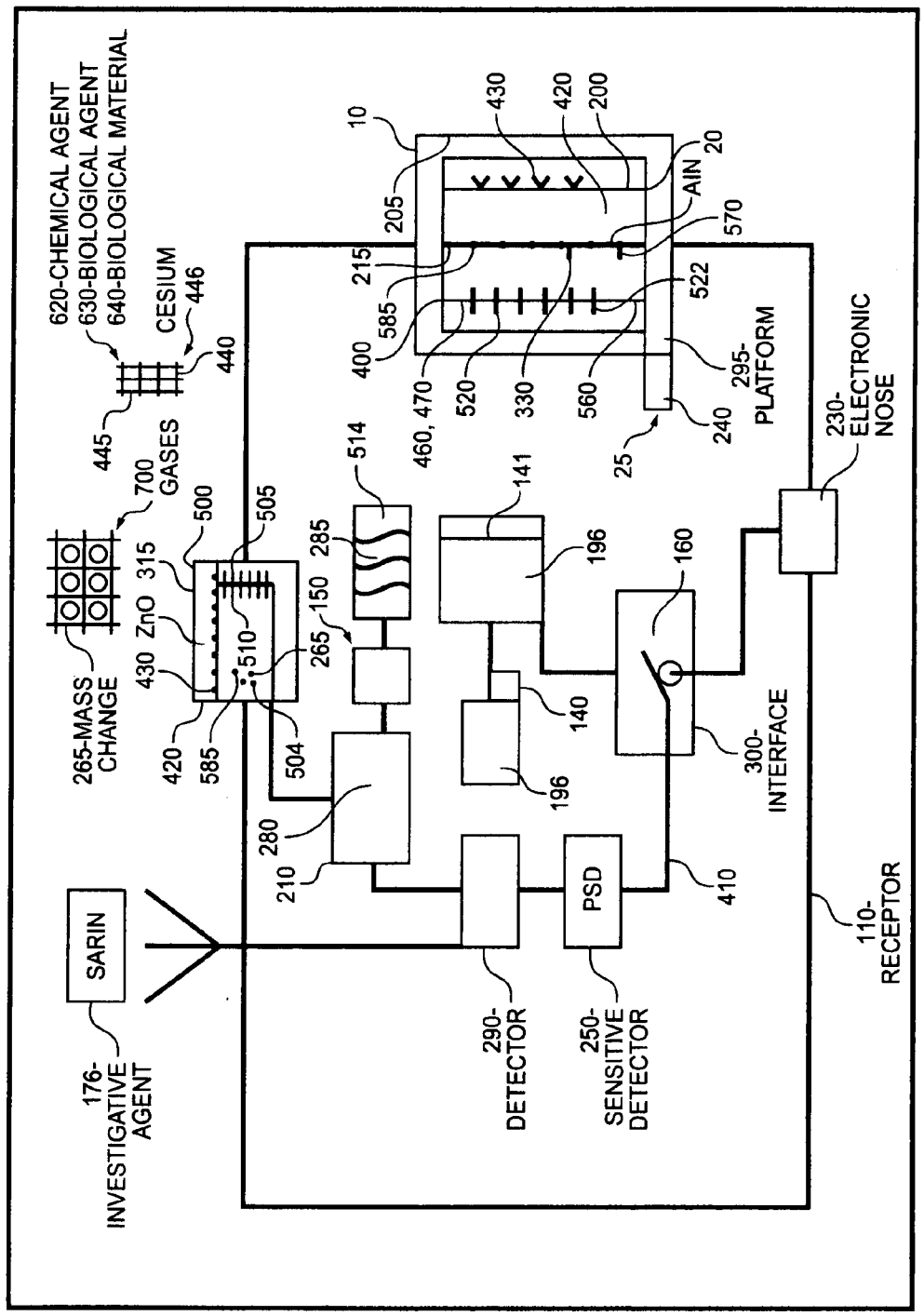
FIG. 4 is seen to represent a piezoelectric and micro electro-mechanical system on a jacket connected to a receptor.

FIG. 4 is seen to show a piezoelectric micro-mechanical system and thin film in the detection system, allowing incorporation of a combination of micro-electro-mechanical systems (420) and thin film (430) technologies into the design of H-LIST detection, enabling the integration of silicon micro-fibered materials (220) and microelectronics circuits (410) into multifunctional sensor arrays (330), fabricated on a sensor in a silicon substrates (205) sensitivity and affixed in the interior of an outfit (10a) fabric or a wearable security jacket (10) to enable detection of biological, chemical, mechanical, and physical parameters of enforceable destructive material. When the sensor is embedded inside the silicon substrate (205) and etched inside the micro-fibered material (220) or other fabric materials, and the microelectronic circuit (410) is integrated into H-LIST device development and interfaced with multiple sensors, it advances pattern recognition techniques in the application of the sensing materials used for the development of homeland security. Allowing the application and implementation of H-LIST, which prescribes advanced sensors for multifunctional applications and designs to enable the integration of other technologies to enhance interactive homeland security by adopting other microprocessor electronics (85) into a digitized system, enabling incorporation wireless mobile detection into biochemical, chemical, or multifunctional sensing through a wearable fashioned outfit (10a) designed to be worn by law enforces, or security officers (35), or other agencies for monitoring biological and chemical gases (700) or other explosive elements within a common environment (60) or for security and global protection.

H-LIST could be transformed into H-LIST.IP Homeland Intelligence systems Technology for International Protection," and will search and process any material of mass destruction such as biological, chemical gas, or other explosive devices in an assigned environment. That is, tiny grains of sensors (200) or (200a) are embedded in a silicon substrate (205) and affixed on a micro-fibered material (220). The micro-fibered material (220) is then affixed on the interior of a regular wearable jacket (10), such that are normally worn by officers, security officers (35), law enforcement officers, military personnel and the like. The tiny grains of sensors (200) are all trained to recognize different gases 700), biological (630), chemical (620), or explosive materials in their wavelike pattern structure, and are intelligently constructed and architect to invisibly run through the silicon substrate (205) in the micro-fibered material (220) in a way that all the tiny grains of sensors (200) or (200a) are coded and wired in the micro-fibered material (220), such that an extended output connector (25)

is exposed out of the micro-fibered material (220) to the side of the outer or inner assembly of the jacket (10) or outfit (10a).

Figure 5:
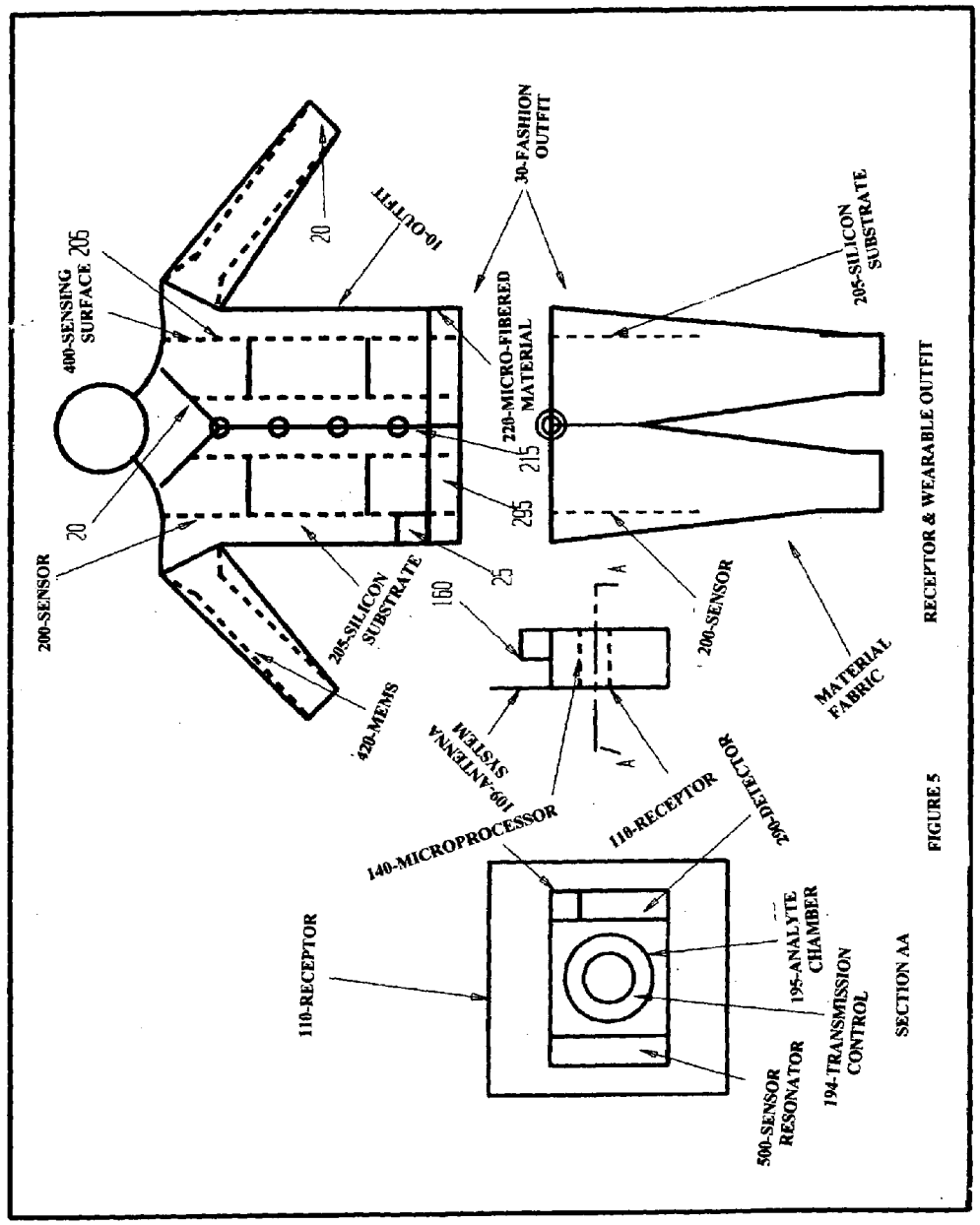
FIG. 5 is seen to represent a receptor and a wearable security outfit. Section AA is a cutout view of the receptor.

A rechargeable receptor (110) is worn on a waist belt (120) and on the waist area (130) of the security officer (35). The receptor (110) has an adapting input connecting end (160) that accepts output from the silicon substrate sensors (205) into the input terminal (160) of the receptor (110). FIG. 5 is seen to show a receptor (110) and a wearable outfit (10a) configured on the officer's body. A silicon micro-fibered material (220) is affixed on a jacket (10). The affixation is in a way that could be easily detached off the jacket (10) during normal cleaning. The silicon micro-fibered material (220) acts as an insulator on the officer's body, and as a detector on its mobile environment (60), permitting intelligent monitoring of such explosives (700) or deadly devices. The sensors (200) run through the interior part of the jacket (10), and the output terminal (25) extends outwardly at the lower side of the jacket (10) such that the extended output connector (25) is connected to the input adaptor (160) of the receptor (110). The receptor (110) is made of microelectronic materials and incorporates an intelligent microprocessor chip (140) that empowers the trained brains of the embedded sensors (200) or (200a) in the silicon micro-fibered material (220), such that the sensors detections of deadly materials or weapons are timely and the analysis and reporting is in milliseconds per real time.

The receptor (110) connects and report to the central security monitoring station (70) through wireless networks (66) or wind towers (71) and remotely empowers the detecting sensors to monitor assigned environments (60) for materials such as radioactive cesium, chemical, biological, explosives, toxic, biochemical, and the like. Such an environment (60) includes, but is not limited to battlefield, office buildings, public recreation areas, transportation equipment, city centers, stadiums, government buildings, airports, schools, tunnels and the like. The application of H-LIST advances the knowledge needed in monitoring anticipatory or suspected terrorists acts and also makes Homeland Intelligence Systems communicative by advancing knowledge and information system's detection of suspected terrorist movements. The application of H-LIST is further integrated in either analog or digital systems or both, with higher degree of processing large information at much higher sensing speed. By incorporating advanced sensing through the multifunctional sensors (215) in the inner detachable lining (20) insulator inside the jacket (10), or an outfit (10a), localized parameters will be detected simultaneously and higher communication signal to noise ratio and good cross sensitivity will be covered by the sensing amplification through the receptor chips (140). The sensors (200), which consist of a detector platform (295), will communicate with the detectors (290) through an active interface means with variable electrical, mechanical, optical, or chemical impedance. The platform (295) will generate electrical output signals or pulses indicative of the detected information and communicate thereof.

As shown in FIG. 6, sensors (200) and (200a) are developed with optimized selectivity and sensitivity, using semiconductor fabrication line in their development process to enable communication of human body responses to environment, such as heart beats or respiratory data reporting. Because of the selectivity and sensitivity of explosive (600) and other chemical or biochemical materials, different materials such as nanocrystalline material could be used in patterning their sensing medium. This material will offer an immersed promise to improving the sensitivity of H-LIST detection. In targeting mixed gases and some odors within a confined location or allocation, other devices such as electronic nose (230) could be used to look for specific patterns or finger prints of the gas mixtures, which may consist of more than one chemical sensor to sense a specific gas and also be trained for a particular pattern recognition system in detecting explosives (600) and other destructive materials. The incorporation of outfit (10a) for sensing and detecting of weapons of mass destruction embraces multiple sensors and mobile detection, such that, with the silicon micro-fibered multifunctional-sensor array (330), gas sensing and other sensing would be based on changes in the surface or near surface oxide conductivity (440), which are caused by the formation of space charge region (445) induced by gas absorption or oxygen vacancies on the surface environment (446).

To enable the accurate operation of H-LIST detection, FIG. 4 shows a schematic of gas sensitivity, which allows the detection of gas concentration, and gas selectivity, which is the detection of specific gases (700) in a mixed gas environment (60), as they are drawn to be of very importance in the smartness of the system in other to prevent the incorporation of intelligent devices such as chips (140), (200a), or semiconductor (142) from being insensitive. In the process of silicon micro-fibered material (220) and the fabrication of microelectronic circuit (410) as shown in FIG. 6 to enhance H-LIST detection, a silicon substrate (205) is micro-machined through a chemical or electrochemical etch technique, employing silicon-to-silicon (460) and or silicon-to-glass and or ceramic wafer bonding (470) to strengthen the micro machining or microelectronics integration to enable multifunctional sensing (215). The silicon-to-glass and or ceramic wafer bonding (470) is seen in FIG. 4 to allow the use of single crystal silicon instead of polycrystalline silicon to improve the design of micro-acoustics and micro optics in the micro-electro-mechanical system (420) and thin film technique (430) to enable the integration of microelectronics circuit (410) and multifunctional sensor (215) into homeland security fashioned jacket (10) or outfit (10a) in H-LIST. Wafer bonding (460) and (470) in single crystal silicon will significantly lower acoustic losses and better optical properties.

Though other bonding method may be used in the microelectronic process, the platform that would allow sensitive electronic monitoring is the piezoelectric sensors (180) shown in FIG. 1 and FIG. 6 or the cantilever sensor (210) shown in FIG. 3 and FIG. 6 both designed in a wearable fashion outfit (30). With these, bulk and surface acoustic wave resonators (500) are used for multifunctional, physical, and chemical sensing, and includes other sensors like viscosity sensors and the like. The resonator-based sensor (500) measures resonance frequency shift such as in surface plasmun resonance spectroscope, caused by mechanical, chemical, or electrical perturbation of the boundary conditions on the active interface (300). These electrical perturbations occur in metal films (543) with different conductivity values deposited on the resonator (500), enabling various loading effects in the liquid and solid media (505), which will damp the oscillations (514) of the resonator (500) and modify the sensor resolution.

The resolution of the sensor is determined by the resonance frequency shift response to the external perturbations, adding the capacity of the monitoring electronics to accurately measure the frequency shift within the detection environment and enabling damping of the oscillation (514), which is caused by the acoustic energy drained when free quartz resonance (510) is brought to contact with solid liquid medium (505). The system uses resonators such as mechanical resonators (500) to measure the frequencies and to enable the design of higher accuracy in sensor sensitivity and selectivity. However, the selectivity process depend on the parameters of the gas absorption and co-absorption mechanism, surface reaction kinetics, and electron transfer to and from the conduction band of the semiconductor (142), which are achieved by enhancing gas absorption or electronic effect in plurality method such as surface modification, and can also be influenced by the addition of metal clusters (520) to increase the sensor sensitivity caused by close coupling between the sensing (400) and catalytic properties (504) of the metal oxide (530). FIG. 4 further shows metal clusters (520), which are added to the sensors (180), (200a) and (200) to increase selectivity and consist of chemical sensitization, which enables metal particles (522) acting as centers for surface-gas absorption and spill over onto the oxide surface (540), enabling reaction with the negatively charged chemisorbed oxygen. The addition of metal clusters (520) enables electronic sensitization resulting from a direct electronic interaction between the oxide surface (540) and the metal particles (522) through metal oxidation and reduction processes.

In other embodiment, thin film coating (430), which is sensitive to the measured parameters of the sensors, is deposited on the resonator (500) to enable changes in the physical or chemical parameters that will change the resonator frequency shift. The resonant-based sensors (180) and (200) will measure resonant frequencies shifts caused by mechanical, electrical perturbations, chemical or biochemical equivalent. With this piezoelectric resonator (500), electrical perturbation will occur in the metal films (543) with different conductivity values deposited on the resonator. When the resonator (500) is immersed in water, it will be deposited in ion-conducting electrolyte. The resolution of the sensors are determined by the resonance frequency shift in response to the external perturbations and the capacity of the monitoring electronics to accurately measure the frequency since H-LIST allows amplification of electronic signals detected by the multifunctional sensors (215). In this, the oxidized particles are reduced, enabling a change in carrier concentration of the semiconductor oxide substrate (560) to enhance sensitivity through doping to modify the carrier concentration and mobility, or through micro structured changes by the reduction of oxide particle sizes.

In all teachings of the H-LIST device, the film processing allows the understanding of thin film deposition processes like chemical vapor condensation or sputtering, and screen-printing or tape casting. As the thin film (430) is deposited on the piezoelectric resonant line (570), additional acoustic shear wave modes that will not couple electrically to fluid are used to avoid heavy loss of acoustic energy. Each film will detect a corresponding gas component. Still in other embodiment, silicon and a non-piezoelectric substrate are used to configure a surface acoustical wave to enable detection selectivity and sensitivity. With this, inter-digital transducers (315) are coated with ZnO, which is a piezoelectric material that could be deposited using reactive magnetron sputtering. The surface acoustic wave line (570), which is enabled when the sensing coating changes its mechanical parameters in the presence of the gas to which partial pressure is measured, will enable the resonant frequency shifts due to the surface acoustic wave propagation velocity. The surface acoustic wave line (570) is coated with passive glass film for calibration, allowing the pattern recognition techniques to be administered and communicated in order to analyze the signals coming from the various sensor arrays (330). The resonator (500) has a maximum conductivity and behaves like a resistor corresponding to a zero phase shift.

In another embodiment, wind current (804) traveling through waves (820), such as radio wave or microwaves are coded and empowered by a wind energy source (830). The operation of the wind energy source (830) is interactive with at least a turbine (840) responsive for emitting matching energies in anticipation of possible energy generated by a combination of chemical or biological agents culminating in weapons of mass destruction. Such weapons of mass destruction include verbal aerial communication between enemy networks such as networks run by (a) terrorist groups. The wind energy source (830) is linked with the wind fiber tower (71) to enable interactive networks spectrum for communication indicative of reaching homeland security broadband networks for local, state, regional and federal first responders through H-LIST. Whereby the outfit enables a platform for detection and is configured with the receptor for providing high resolution chemical, biological and explosive detection date and other critical data to first responders.

In another embodiment, a paste or ink (585) is printed on a suitable substrate with two-stage heat treatment to form a dense layer with a favorable structure. In yet another embodiment, the paste (585), which is of powder mixed with an organic medium and a binder, collaborate the correct theological properties to deposit layers of sensor materials on the substrate.

The paste (585), which contains nanoparticles, is deposited in different substrates and heated at various temperatures to obtain the required dimension of the film (430), enabling reactive sputtering processes or vapor deposition process that is superior for the use of H-LIST in mobile detection, monitoring and security. Still in another embodiment, a low temperature and pressure deposited aluminum Nitride "AlN" thin film (316) is used to integrate with microelectronic devices and sensors with conventional photolithographic patterning technique, embedded in a silicon substrate (205), and etched on a micro-fibered fabric material (220) for the design of outfit (10a). Other materials that are not mentioned in the invention could be used as a fabric to etch the embedded sensor on the silicon substrate (205). A flexural plate wave gravimeter sensor fabricated from SOI wafers will enable the aluminum nitride "AlN" (316) to be deposited on its surface, allowing the integrated digital transducers (315) to act on the piezoelectric aluminum nitride layer to enable the lunching and detection of plate waves on a thin silicon membrane (190), which is coated with binding site-specific polymers, such that a change in the silicon membrane resonance frequencye will detect a change in the piezoelectric crystal mass (265) as a result of a subsequent change in the membrane mass (195).

The binding of the associated antibody/antigen caused by specific recognition would result in mass increase and decrease in frequency. The change of frequency reflects the presence and amount of the targets. In another embodiment, the piezoelectric AlN thin film (316) is deposited on a glass and or ceramic substrates and embedded in a silicon material to improve the flexibility of the sensors (180), (200), and (200a) etched in a micro-fibered material (220) to enable a lining fabric, allowing specific designs that could be prescribed for any fashion outfit wearable for security monitoring of deadly gases (700) and explosives (600). Achievement is obtained through manipulation of the structure of the film by controlling the deposition parameter precisely. However, both nanopowder and nanostructured film are utilized in the process. Nanostructured materials are the essentials to achieving high gas sensitivity, but the technique requires desired oxide composition with a specific dopant and few processing steps. Oxide materials are made more sensitive by introducing dopants, which have unique gas absorption characteristics and utilizes materials with specific catalytic properties to enhance gas sensitivity.

Figure 12A:
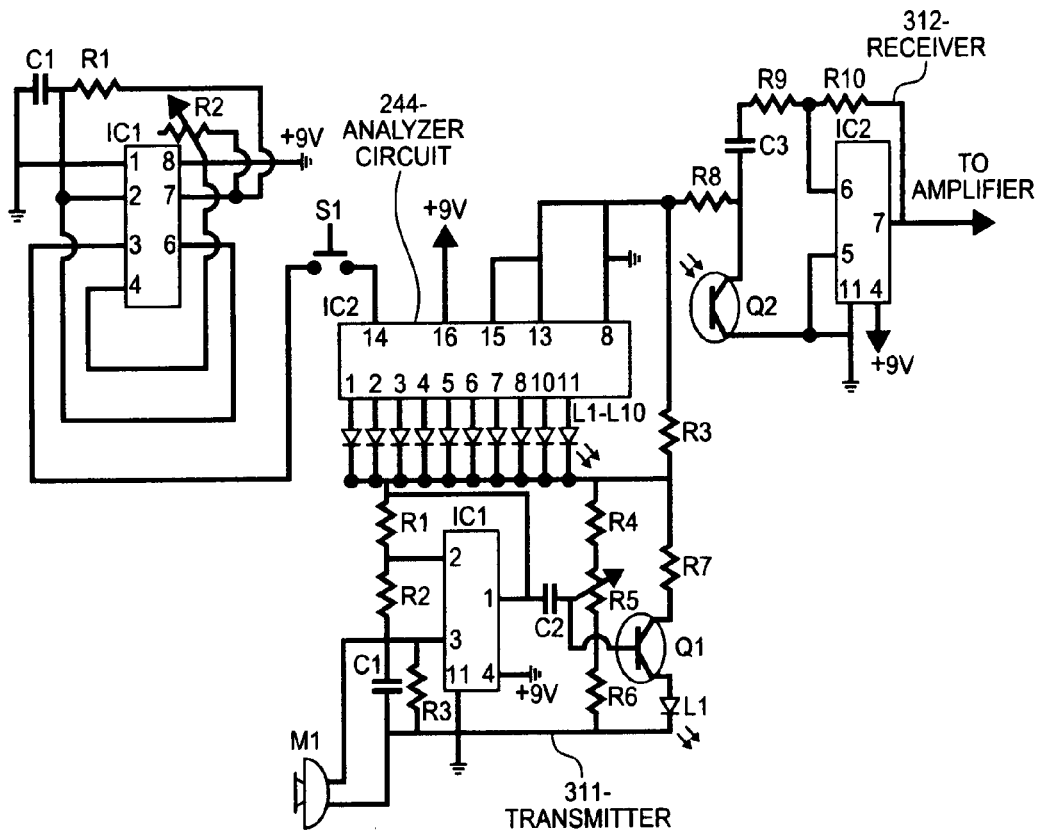
FIG. 12 is seen to represent a circuit diagram for receptor's random switching generator with receivers and transmitters.
Figure 12B:
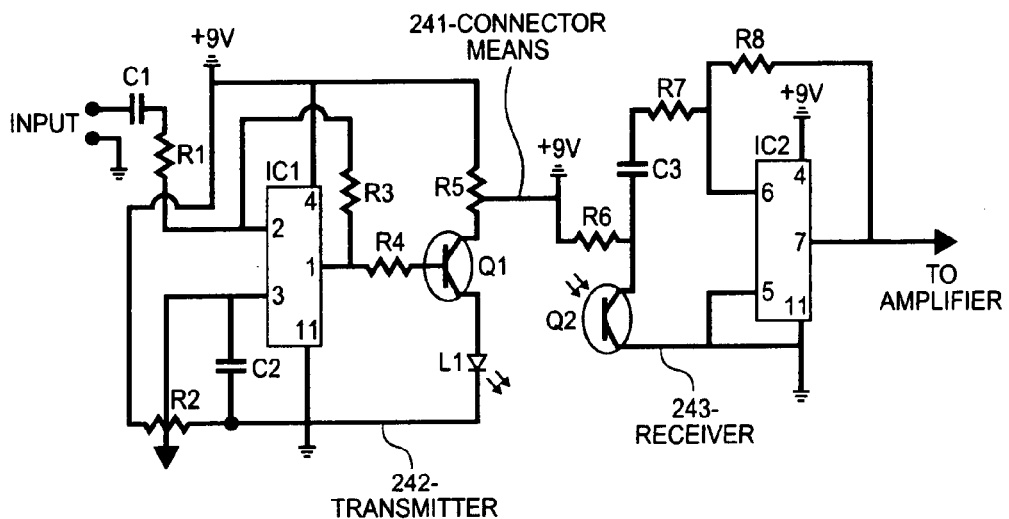
Figure 15A:
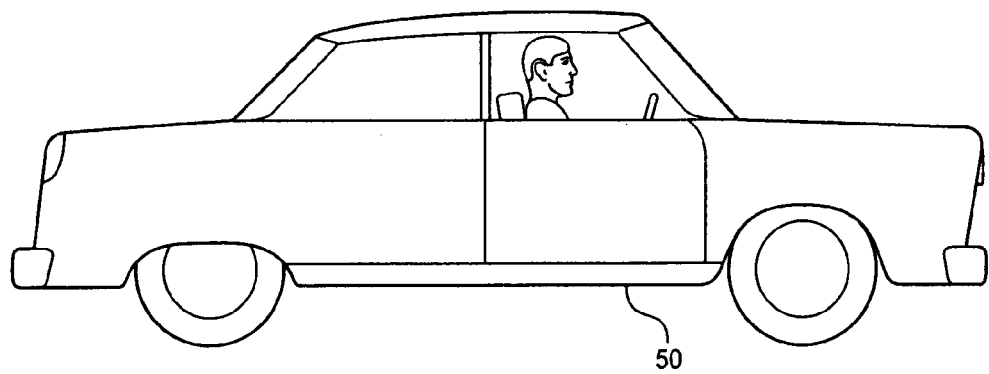
FIG. 15 is seen to represent military personnel whose uniforms have detected a vehicle that is equipped with explosives
Figure 15B:
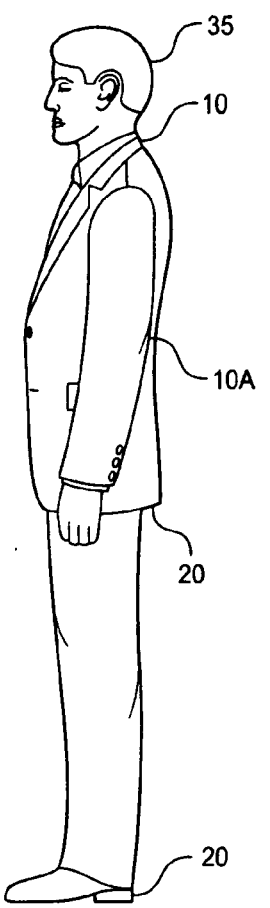
Figure 15C:
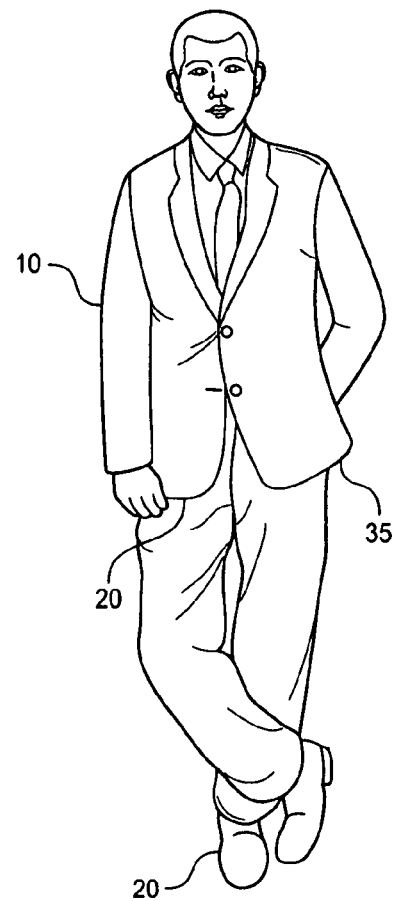
Figure 16A:
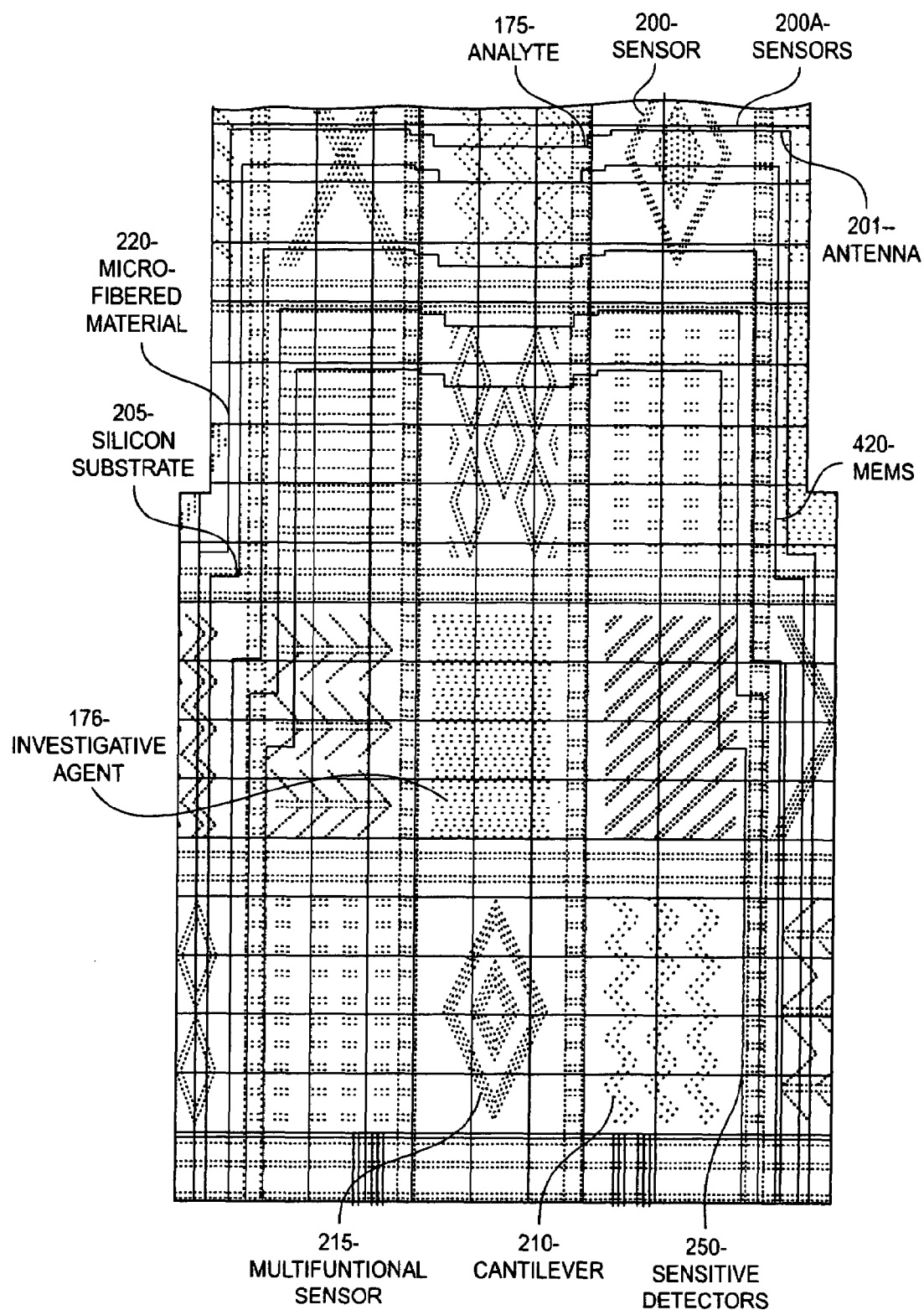
FIG. 16 is seen to represent a planned outline of the micro-fabric material with the embedded sensors.
Figure 16B:
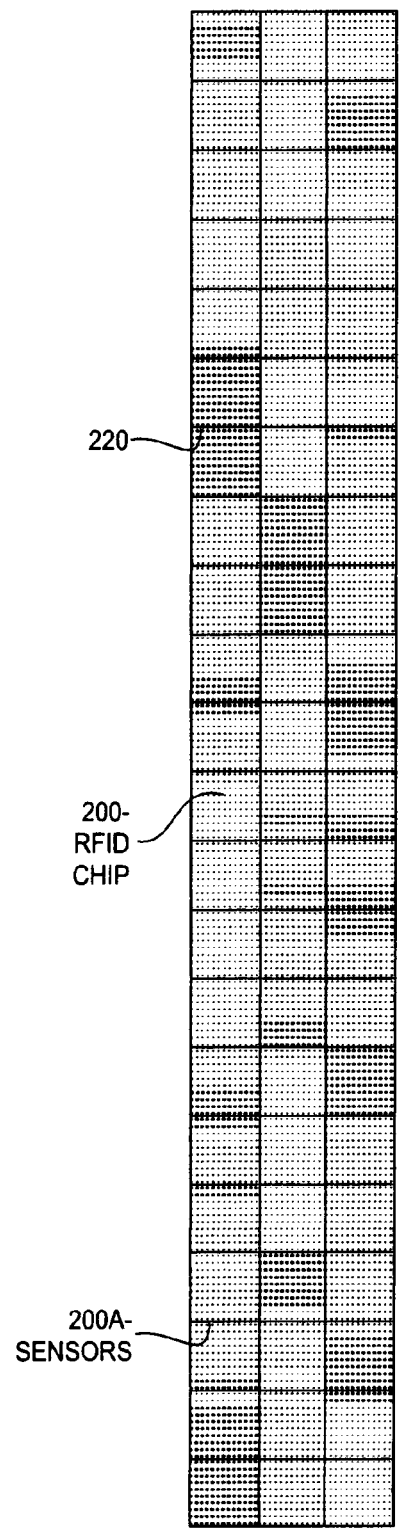

The drawings clearly outline the scope and embodiment of present invention. As per FIG. 12, the following components are further explained.

1C1=CPU
1C2=RFID Chip reader
L1+L2=LED
S1=ASPDT "Automatic momentary single pole double throw" switch, for transmitting and receiving signals
C1=Electrolytic capacitor
C2=imf capacitor
C3=imf capacitor
Q1=Infrared or general purpose silicon transistor
Q2=Phototransistor detector
L1=Infrared LED emitter
M1=speaker/microphone
R1 through R10=Resistors It is to be understood that the scope of the present invention is not limited to the above description, but encompasses the following claims:

What is claimed is:

1. A device for Homeland intelligence systems technology to enable detection of and protection against weapons of mass destruction, comprising:
    at least a sensor means embedded in at least a silicon substrate and etched/fused in at least a micro-fibered material worn on a person, in communication with an effective detection platform;
    said detection platform embedded in the silicon substrate comprising an interactive monitoring means operatively configured to relay to at least a communication means located in a receptor positioning proximately to the detection platform, wherein said detection platform further enables post-use detection of deadly weapons in a monitored environment assignment;
    means configured to empower said detection platform;
    said receptor comprising means for analyzing detection signals transmitted from the sensor means;
    said communication means communicatively configured with said detection platform for enabling detection and interactive communication; and
    said communication means further enabling a wireless communication network with a transmitter means and a receiver means, operatively configured to enable communicating said analyzed signals of deadly weapons to a control center, including at least a homeland security agency.

2. A device for Homeland intelligence systems technology of claim 1, wherein said sensor means comprises a plurality of sensors, each said plurality of sensors configured to enable at least a specific detection of deadly weapons, and wherein the communication means further configured to produce a real-time alert when a concealed object and or weapon of mass destruction is detected.

3. A device for Homeland intelligence systems technology of claim 2, wherein said communications means further comprising means for transmitting and receiving analog and/or digital signals of varying frequencies.

4. A device for Homeland intelligence systems technology of claim 3, wherein said sensor means comprises nano-sensors, bringing signals that contain at least chemical targets into contact with said detection platform, thereby allowing at least a chemical target to be bound to a discrete region of said sensor means.

5. A device for Homeland intelligence systems technology of claim 4, wherein said nano-sensors further include at least MEMS and at least an RFID code-able chip, said detection platform further comprising providing a substrate across which is distributed an array of discrete regions, said discrete regions having membranes that pass through the sensor means.

6. A device for Homeland intelligence systems technology of claim 5, wherein said sensor means provide an optical radiation corresponding to a first wavelength emitted from at least one of the discrete region of said nano-sensor.

7. A device for Homeland intelligence systems technology of claim 6, wherein said discrete regions of said nano-sensors have membranes passing through the sensor means responsive for analyzing data transmission.

8. A device for Homeland intelligence systems technology of claim 7, wherein said discrete regions of said nano-sensors further comprise a first cleansing of the affinity column for extracting at least an analyte of dissolved and/or suspended material other than the bound analyte.

9. A device for Homeland intelligence systems technology of claim 8, wherein said discrete regions of said nano-sensors further comprise a second releasing of the analyte from the affinity column for providing the analyte with a measurable fluorescence when the analyte does not have a measurable natural fluorescence said discrete region further comprises a reflecting layer to enhance sensitivity of detection.

10. A device for Homeland intelligence systems technology of claim 9, wherein said sensor means enables detection of a human heartbeat and respiratory system within a monitoring environment and or battlefield assignment.

11. A device for Homeland intelligence systems technology of claim 10, wherein said sensor means determines whether a person is carrying a concealed object by conducting a test in which a first characteristic of a first dielectric constant associated with the person is determined, and a second characteristic of a second dielectric constant associated with the weapon of mass destruction is determined.

12. A device for Homeland intelligence systems technology of claim 11, wherein said sensor means further includes method for transforming the effects of electrochemical interaction with an analyte electrode into useful signal communication to said control center.

13. A device for Homeland intelligence systems technology of claim 12, wherein said analyte of said sensor means comprises at least a metal oxide and/or semiconductor gas sensor.

14. A device for Homeland intelligence systems technology of claim 13, wherein said sensor means further includes at least a transmitter for transmitting detection signals to enable interactive wireless communication with said control center, said re-enforced micro-fibered material having excellent electrical properties for enabling thermal control and for re-enforcing sensitivity of detection.

15. A device for Homeland intelligence systems technology of claim 14, wherein said detection platform is operatively configured to detect a concealed weapon, including weapons in a gaseous phase, a liquid phase, a solid phase, or an applied explosive phase, and is further configured to produce real-time alert when a weapon of mass destruction is detected.

16. A device for Homeland intelligence systems technology of claim 15, wherein said detection platform comprises a temperature detector, a contextual object detector, and at least a speech detector, further comprising providing a substrate across which is distributed an array of discrete regions, said discrete regions having membranes that pass through the sensor means, and responsible for data transmission.

17. A device for Homeland intelligence systems technology of claim 16, wherein said detection platform is further configured to detect selected sounds, un-parallel wave motion, biological agents, chemical agents, nuclear agents, radiological agents, and at least a Q factor responsive for environmental pressure change.

18. A device for Homeland intelligence systems technology of claim 17, wherein said detection platform includes a mobile detection means configured to detect objects concealed in a person, a vehicle, or a vicinity.

19. A device for Homeland intelligence systems technology of claim 18, wherein said mobile detection means comprises a bistatic radar.

20. A device for Homeland intelligence systems technology of claim 19, further comprising a silicon substrate and a micro-fiber material on said sensor means for re-enforcing the effectiveness of said detection platform.

21. A device for Homeland intelligence systems technology of claim 20, wherein said silicon substrate and/or said micro-fiber material have excellent electrical properties.

22. A device for Homeland intelligence systems technology of claim 21, wherein said micro-fiber material comprises transistorized switches etched or fused within it to enable thermal adjustment to environmental change.

23. A device for Homeland intelligence systems technology of claim 22, wherein said communication means further includes a receiving means, including at least an RFID chip operatively configured with an fm receiver.

24. A device for Homeland intelligence systems technology of claim 23, wherein said communication means is configured with a memory and data storage means and communicatively connected to a control center.

25. A device for Homeland intelligence systems technology of claim 24, wherein said communication means further includes means for transmitting and receiving analog and digital signals of varying frequencies.

26. A device for Homeland intelligence systems technology of claim 25, wherein said communication means is configured to convert signals from said sensor means and said detection platform into useful analytical signals and send them to a receiving means at said control center.

27. A device for Homeland intelligence systems technology of claim 26, wherein said communication means further comprises means for audiovisual communication and speaker means for outputting human voice auditory message to personnel conducting security monitoring and or battlefield engagement.

28. A device for Homeland intelligence systems technology of claim 27, wherein said communication means further comprises a first operational amplifier circuit configured with at least a characteristic for converting the electrical current from the detection platform into a pulse.

29. A device for Home-land intelligence systems technology of claim 28, wherein said transmitter means is responsive for transmitting signals from said communication means to said receiving means at said control center.

30. A device for Homeland intelligence systems technology of claim 29, wherein said receiving means is coupled to an antenna and sensor means further comprises pattern recognition technique.

31. A device for Homeland intelligence systems technology of claim 30, wherein said antenna means is operatively configured with said detection platform and receiving means for receiving and outputting detection signals, said pattern recognition technique further includes at least an optical character recognition technique.

32. A device for Homeland intelligence systems technology of claim 31, wherein said antenna of said receiving means comprises an end-fire waveguide antenna and the detection signal further comprises a frequency stepped signal, further includes means for protecting at least a human body from body bacterial.

33. A device for Homeland intelligence systems technology of claim 32, wherein said receiving means further comprises means for transforming changes in optical phenomena due to at least an interaction of an analyte with a receptor part indicative of a sensed agent and/or explosives, said means outputting micro-impulse waves, further comprises at least a radio frequency identification "RFID" further responsive for measuring a change in electrical properties caused by the interaction.

34. A device for Homeland intelligence systems technology of claim 33, wherein said sensor means comprises at least a proximity sensor configured with said detection platform, said receiving means further comprising means for transforming at least a mass change at a modified surface into a change of property of a support material.

35. A device for Homeland intelligence systems technology of claim 34, wherein said detection platform further comprises means for detecting data characteristics traveling through waves and said receiving means receiving said data responsive for sharing said data characteristics with at least a network structure.

36. A device for Homeland intelligence systems technology of claim 35, wherein said data characteristics comprises audio and/or data from anticipatory sensing of at least a weapon of mass destruction, and wherein at least one of the antenna means comprises at least an RFID chip and/or a spiral antenna.

37. A device for Homeland intelligence systems technology of claim 36, wherein said data characteristics comprises data commonly shared with at least a network computer during an emergency, and wherein said network computer comprises at least a handheld device and said discrete regions further includes at least a reflecting layer to enhance sensitivity of detection.

38. A device for Homeland intelligence systems technology of claim 37, wherein said data characteristics further comprises at least foreign objects in at least wind waves, and wherein said wind waves include at least said micro-impulse waves.

39. A device for Homeland intelligence systems technology of claim 38, wherein said data characteristics comprises contextual characteristics data of said weapons of mass destruction and said micro-fibered material comprises outfit configured with said sensor means for receiving signals.

40. A device for Homeland intelligence systems technology of claim 39, wherein said outfit comprises at least a uniform commonly worn by armed personnel, including CIA, FBI, SECRET SERVICE, POLICE, CUSTOMS, and GUARDS.

41. A device for Homeland intelligence systems technology of claim 40, further comprises at least outfit commonly worn by unarmed personnel, including Doctors, nurses, and hostesses, pilots of transit vehicles, pilots of mail delivery vehicles, laboratory personnel, and security guards.

42. A mobile homeland security system for monitoring terrorist activities and enemy line in a battlefield comprising:
- a portable wearable outfit enabling detection of and protection against weapons of mass destruction, said portable wearable outfit comprising:
- a processing means for receiving and processing analog and digital signals;
- a pattern of recognition technique in communication with said processing means for determining pattern common to deployment of weapons of mass destruction;
- a system of sensors in communication with processing means and pattern of recognition technique comprising means for detecting deployment of biological, chemical, explosive, or radioactive agents;
- said system of sensors embedded in a silicon substrate and etched in a micro-fibered material located on said portable wearable outfit; and
- a control center in communication with said processing means broadcasting emergency conditions to personnel monitoring assigned environment.

43. A wearable protection and monitoring outfit and system for protecting a site and detecting weapons of mass destruction, comprising:
- a sensor means embedded in a silicon substrate and etched in a micro-fiber material on the wearable protection and monitoring outfit for detecting deployment of biological, chemical, explosive or radioactive agents;
- a detection means for analyzing signal communication from said sensor means, comprising:
- an antenna coupled to said sensor means;
- a transmitter in communication with said detection means enabling analyzed data transmission to a control means;
- a conversion means within said control means for receiving said analyzed data transmission and analyzing said data into a wind pattern representation of a weapon of mass destruction frequency.

44. A wearable protection and monitoring outfit and system for protecting a site and detecting weapons of mass destruction, comprises:
- a sensing means;
- at least a cell means;
- a detection means;
- a communication means, in communication with said detection means and said at least a cell means, comprising at least a first ship means;
- a control means in communication with said communication means;
- said communication means in communication with said detection means; and
- said control means, comprising a ship disposed with at least a wind tunnel configured with at least a propeller operatively disposed with a turbine operatively connected to at least a second ship means, a cell means, wherein said at least first ship means and said at least second sip means communicatively enable energy upgrade for said outfit and said system through wind energy source means.

45. A wearable protection and monitoring outfit of claim 44, wherein said at least a first ship means or wherein said at least a second ship means comprises at least a battery cell.

* * * * *